(12) United States Patent
Pantages et al.

(10) Patent No.: US 8,083,754 B2
(45) Date of Patent: Dec. 27, 2011

(54) VASCULAR SUTURING DEVICE WITH NEEDLE CAPTURE

(75) Inventors: Anthony J. Pantages, San Jose, CA (US); Brian Ellingwood, Sunnyvale, CA (US); Erik Walberg, Redwood City, CA (US)

(73) Assignee: Abbott Laboratories, Abbott Park, IL (US)

( * ) Notice: Subject to any disclaimer, the term of this patent is extended or adjusted under 35 U.S.C. 154(b) by 1394 days.

(21) Appl. No.: 11/199,496

(22) Filed: Aug. 8, 2005

(65) Prior Publication Data

US 2007/0032798 A1   Feb. 8, 2007

(51) Int. Cl.
*A61B 17/04* (2006.01)
*A61B 17/12* (2006.01)

(52) U.S. Cl. .......................................................... 606/144

(58) Field of Classification Search .................. 606/144, 606/139, 145–147, 149–150, 213, 232, 148; 112/171
See application file for complete search history.

(56) References Cited

U.S. PATENT DOCUMENTS

| | | |
|---|---|---|
| 312,408 A | 2/1885 | Wackerhagen |
| 597,165 A | 1/1898 | Hall |
| 659,422 A | 10/1900 | Shidler |
| 989,231 A | 4/1911 | Davis |
| 1,574,362 A | 9/1922 | Callahan |
| 1,625,602 A | 4/1927 | Gould et al. |
| 1,940,351 A | 3/1933 | Howard |
| 2,012,776 A | 8/1935 | Roeder |
| 2,131,321 A | 10/1937 | Hart |
| 2,108,206 A | 2/1938 | Meeker |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,595,086 A | 11/1948 | Larzelere |
| 2,588,589 A | 3/1952 | Tauber |
| 2,610,631 A | 9/1952 | Calicchio |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |

(Continued)

FOREIGN PATENT DOCUMENTS

DE           912619         5/1954

(Continued)

OTHER PUBLICATIONS

U.S. Appl. No. 11/199,338, Mail Date Apr. 23, 2008, Office Action.

(Continued)

*Primary Examiner* — Gary Jackson
*Assistant Examiner* — Lindsey Bachman
(74) *Attorney, Agent, or Firm* — Workman Nydegger; Randy Shen

(57) ABSTRACT

A surgical device of suturing vascular vessels is described, as well as methods for suturing tissue employing the surgical device. The device includes at least one needle advanceable through tissue and into a needle capture element within a distal end of the surgical device to draw lengths of suture material which can then be used to close various puncture wounds, particularly in vascular tissue.

23 Claims, 11 Drawing Sheets

U.S. PATENT DOCUMENTS

| | | |
|---|---|---|
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,587,115 A | 6/1971 | Shiley |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,814,104 A | 6/1974 | Irnich et al. |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,908,662 A | 9/1975 | Razgulov et al. |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,011,872 A | 3/1977 | Komiya |
| 4,018,228 A | 4/1977 | Goosen |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,501,276 A | 2/1985 | Lombardi |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleishhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Orvil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,830,002 A | 5/1989 | Semm |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yo on |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,287 A | 3/1993 | Fournier et al. |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,471 A | 6/1993 | Burkhart |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,237,996 A | 8/1993 | Waldman |
| 5,242,427 A | 9/1993 | Bilweis |
| 5,250,033 A | 10/1993 | Evansetal |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bognato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,312,423 A | 5/1994 | Rosenbluth et al. |
| 5,318,578 A | 6/1994 | Hasson |
| 5,320,629 A | 6/1994 | Noda et al. |
| 5,320,632 A | 6/1994 | Heidmueller |
| 5,330,445 A | 7/1994 | Haaga |
| 5,330,491 A | 7/1994 | Walker et al. |
| 5,334,217 A | 8/1994 | Das |
| 5,336,229 A | 8/1994 | Noda |

| | | | | | |
|---|---|---|---|---|---|
| 5,336,230 A | 8/1994 | Leichtling et al. | 5,545,178 A | 8/1996 | Kensey et al. |
| 5,336,231 A | 8/1994 | Adair | 5,545,180 A | 8/1996 | Le et al. |
| 5,342,369 A | 8/1994 | Harryman, II | 5,549,618 A | 8/1996 | Fleenor et al. |
| 5,353,974 A | 10/1994 | Brinkerhoff et al. | 5,549,631 A | 8/1996 | Bonutti |
| 5,354,279 A | 10/1994 | Hofling | 5,554,162 A | 9/1996 | DeLange |
| 5,354,312 A | 10/1994 | Brinkerhoff et al. | 5,562,684 A | 10/1996 | Kammerer |
| 5,364,407 A | 11/1994 | Poll | 5,562,686 A | 10/1996 | Sauer et al. |
| 5,364,408 A | 11/1994 | Gordon | 5,562,688 A | 10/1996 | Riza |
| 5,368,595 A | 11/1994 | Lewis | 5,562,728 A | 10/1996 | Lazarus et al. |
| 5,368,601 A | 11/1994 | Sauer et al. | 5,567,435 A | 10/1996 | Hubbell et al. |
| 5,374,275 A | 12/1994 | Bradley et al. | 5,569,269 A | 10/1996 | Hart et al. |
| 5,374,278 A | 12/1994 | Chesterfield et al. | 5,569,271 A | 10/1996 | Hoel |
| 5,376,096 A | 12/1994 | Foster | 5,571,120 A | 11/1996 | Yoon |
| 5,383,896 A | 1/1995 | Gershony et al. | 5,573,540 A | 11/1996 | Yoon |
| 5,383,905 A | 1/1995 | Golds et al. | 5,584,842 A | 12/1996 | Fogarty et al. |
| 5,385,569 A | 1/1995 | Swor | 5,591,177 A | 1/1997 | Lehrer |
| 5,387,221 A | 2/1995 | Bisgaard | 5,591,179 A | 1/1997 | Edelstein |
| 5,387,227 A | 2/1995 | Grice | 5,591,206 A | 1/1997 | Moufarrege |
| 5,391,176 A | 2/1995 | de la Torre | 5,593,421 A | 1/1997 | Bauer |
| 5,391,182 A | 2/1995 | Chin | 5,603,718 A | 2/1997 | Xu |
| 5,395,332 A | 3/1995 | Ressemann et al. | 5,607,435 A | 3/1997 | Sachdeva et al. |
| 5,395,349 A | 3/1995 | Quiachon et al. | 5,609,597 A | 3/1997 | Lehrer |
| 5,397,310 A | 3/1995 | Chu et al. | 5,611,794 A | 3/1997 | Sauer et al. |
| 5,397,325 A | 3/1995 | Della Badia et al. | 5,613,974 A | 3/1997 | Andreas et al. |
| 5,397,326 A | 3/1995 | Mangum | 5,613,975 A | 3/1997 | Christy |
| 5,403,329 A | 4/1995 | Hinchcliffe | 5,624,446 A | 4/1997 | Harryman, II |
| 5,403,330 A | 4/1995 | Tuason | 5,626,588 A | 5/1997 | Sauer et al. |
| 5,403,331 A | 4/1995 | Chesterfield et al. | 5,643,289 A | 7/1997 | Sauer et al. |
| 5,403,338 A | 4/1995 | Milo | 5,643,295 A | 7/1997 | Yoon |
| 5,405,352 A | 4/1995 | Weston | 5,643,318 A | 7/1997 | Tsukernik et al. |
| 5,411,481 A | 5/1995 | Allen et al. | 5,647,372 A | 7/1997 | Tovey et al. |
| 5,413,571 A | 5/1995 | Katsaros et al. | 5,649,959 A | 7/1997 | Hannam et al. |
| 5,417,684 A | 5/1995 | Jackson et al. | 5,662,664 A | 9/1997 | Gordon et al. |
| 5,417,699 A | 5/1995 | Klein et al. | 5,669,917 A | 9/1997 | Sauer et al. |
| 5,419,765 A | 5/1995 | Weldon et al. | 5,672,174 A | 9/1997 | Gough et al. |
| 5,425,705 A | 6/1995 | Evard et al. | 5,674,231 A | 10/1997 | Green et al. |
| 5,425,737 A | 6/1995 | Burbank et al. | 5,676,689 A | 10/1997 | Kensey et al. |
| 5,425,740 A | 6/1995 | Hutchinson, Jr. | 5,693,061 A | 12/1997 | Pierce et al. |
| 5,431,666 A | 7/1995 | Sauer et al. | 5,700,273 A | 12/1997 | Buelna et al. |
| 5,433,700 A | 7/1995 | Peters | 5,707,379 A | 1/1998 | Fleenor et al. |
| 5,452,733 A | 9/1995 | Sterman et al. | 5,713,899 A | 2/1998 | Marnay et al. |
| 5,454,822 A | 10/1995 | Schob et al. | 5,713,910 A | 2/1998 | Gordon et al. |
| 5,454,834 A | 10/1995 | Boebel et al. | 5,716,369 A | 2/1998 | Riza |
| 5,458,574 A | 10/1995 | Machold et al. | 5,720,574 A | 2/1998 | Barella |
| 5,462,560 A | 10/1995 | Stevens | 5,720,757 A | 2/1998 | Hathaway et al. |
| 5,462,561 A | 10/1995 | Voda | 5,722,981 A | 3/1998 | Stevens |
| 5,464,426 A | 11/1995 | Bonutti | 5,725,552 A | 3/1998 | Kotula et al. |
| 5,466,241 A | 11/1995 | Leroy et al. | 5,728,109 A | 3/1998 | Schulze et al. |
| 5,470,338 A | 11/1995 | Whitfield et al. | 5,728,114 A | 3/1998 | Evans et al. |
| 5,474,568 A * | 12/1995 | Scott ............................ 606/144 | 5,728,133 A | 3/1998 | Kontos |
| 5,476,469 A | 12/1995 | Hathaway et al. | 5,728,143 A | 3/1998 | Gough et al. |
| 5,476,470 A | 12/1995 | Fitzgibbons, Jr. | 5,728,151 A | 3/1998 | Garrison et al. |
| 5,478,309 A | 12/1995 | Sweezer et al. | 5,741,276 A | 4/1998 | Poloyko et al. |
| 5,478,353 A | 12/1995 | Yoon | 5,741,280 A | 4/1998 | Fleenor |
| 5,478,354 A | 12/1995 | Tovey et al. | 5,746,755 A | 5/1998 | Wood et al. |
| 5,480,407 A | 1/1996 | Wan et al. | 5,749,890 A | 5/1998 | Shaknovich |
| 5,486,190 A | 1/1996 | Green | 5,755,727 A | 5/1998 | Kontos |
| 5,489,295 A | 2/1996 | Piplani et al. | 5,759,188 A | 6/1998 | Yoon |
| 5,492,119 A | 2/1996 | Abrams | 5,759,189 A | 6/1998 | Ferragamo et al. |
| 5,496,332 A | 3/1996 | Sierra et al. | 5,766,183 A | 6/1998 | Sauer |
| 5,507,744 A | 4/1996 | Tay et al. | 5,766,186 A | 6/1998 | Faraz et al. |
| 5,507,755 A | 4/1996 | Gresl et al. | 5,766,217 A | 6/1998 | Christy |
| 5,507,757 A | 4/1996 | Sauer et al. | 5,769,862 A | 6/1998 | Kammerer et al. |
| 5,507,758 A | 4/1996 | Thomason et al. | 5,779,719 A | 7/1998 | Klein et al. |
| 5,509,902 A | 4/1996 | Raulerson | 5,782,860 A | 7/1998 | Epstein et al. |
| 5,520,655 A | 5/1996 | Davila et al. | 5,782,861 A | 7/1998 | Cragg et al. |
| 5,520,665 A | 5/1996 | Fleetwood | 5,792,151 A | 8/1998 | Heck et al. |
| 5,520,691 A | 5/1996 | Branch | 5,792,152 A | 8/1998 | Klein et al. |
| 5,520,702 A | 5/1996 | Sauer et al. | 5,797,928 A | 8/1998 | Kogasaka |
| 5,527,321 A | 6/1996 | Hinchliffe | 5,797,929 A | 8/1998 | Andreas et al. |
| 5,527,322 A | 6/1996 | Klein et al. | 5,799,661 A | 9/1998 | Boyd et al. |
| D372,310 S | 7/1996 | Hartnett | 5,810,849 A | 9/1998 | Kontos |
| 5,531,700 A | 7/1996 | Moore et al. | 5,810,850 A | 9/1998 | Hathaway et al. |
| 5,536,267 A | 7/1996 | Edwards | 5,814,069 A | 9/1998 | Schulze et al. |
| 5,536,273 A | 7/1996 | Lehrer | 5,817,113 A | 10/1998 | Gifford, III et al. |
| 5,540,701 A | 7/1996 | Sharkey et al. | 5,820,631 A | 10/1998 | Nobles |
| 5,540,703 A | 7/1996 | Barker, Jr. et al. | 5,824,010 A | 10/1998 | McDonald |
| 5,540,704 A | 7/1996 | Gordon et al. | 5,824,111 A | 10/1998 | Schall et al. |
| 5,545,171 A | 8/1996 | Sharkey et al. | 5,830,125 A | 11/1998 | Scribner et al. |

| | | | | | | |
|---|---|---|---|---|---|---|
| 5,836,955 | A | 11/1998 | Buelna et al. | 6,428,472 B1 | 8/2002 | Haas |
| 5,836,956 | A | 11/1998 | Buelna et al. | 6,428,549 B1 | 8/2002 | Kontos |
| 5,846,253 | A | 12/1998 | Buelna et al. | 6,436,109 B1 | 8/2002 | Kontos |
| 5,848,714 | A | 12/1998 | Robson et al. | 6,443,963 B1 | 9/2002 | Baldwin et al. |
| 5,855,576 | A | 1/1999 | LeVeen et al. | 6,451,031 B1 | 9/2002 | Kontos |
| 5,855,585 | A | 1/1999 | Kontos | 6,461,366 B1 | 10/2002 | Seguin |
| 5,860,963 | A | 1/1999 | Azam et al. | 6,511,489 B2 | 1/2003 | Field et al. |
| 5,860,990 | A | 1/1999 | Nobles et al. | 6,517,498 B1 | 2/2003 | Burbank et al. |
| 5,860,991 | A | 1/1999 | Klein et al. | 6,517,553 B2 | 2/2003 | Klein et al. |
| 5,861,005 | A | 1/1999 | Kontos | 6,533,812 B2 | 3/2003 | Swanson et al. |
| 5,871,490 | A | 2/1999 | Schulze et al. | 6,551,330 B1 | 4/2003 | Bain et al. |
| 5,871,502 | A | 2/1999 | Suryadevara | 6,558,399 B1 | 5/2003 | Isbell et al. |
| 5,873,876 | A | 2/1999 | Christy | 6,562,052 B2 | 5/2003 | Nobles et al. |
| 5,876,411 | A | 3/1999 | Kontos | 6,569,159 B1 | 5/2003 | Edwards et al. |
| 5,897,487 | A | 4/1999 | Ouchi | 6,569,185 B2 | 5/2003 | Ungs |
| 5,897,564 | A | 4/1999 | Schulze et al. | 6,572,629 B2 | 6/2003 | Kalloo et al. |
| 5,902,311 | A | 5/1999 | Andreas et al. | 6,610,072 B1 | 8/2003 | Christy et al. |
| 5,904,597 | A | 5/1999 | Doi et al. | 6,623,509 B2 | 9/2003 | Ginn |
| 5,904,690 | A | 5/1999 | Middleman et al. | 6,623,510 B2 | 9/2003 | Carly et al. |
| 5,904,697 | A | 5/1999 | Gifford, III et al. | 6,632,237 B2 | 10/2003 | Ben-David et al. |
| 5,906,631 | A | 5/1999 | Imran | 6,641,592 B1 | 11/2003 | Sauer et al. |
| 5,919,207 | A | 7/1999 | Taheri | 6,663,655 B2 | 12/2003 | Ginn et al. |
| 5,921,994 | A | 7/1999 | Andreas et al. | 6,676,685 B2 | 1/2004 | Pedros et al. |
| 5,928,266 | A | 7/1999 | Kontos | 6,689,051 B2 | 2/2004 | Nakada et al. |
| 5,951,547 | A | 9/1999 | Gough et al. | 6,695,867 B2 | 2/2004 | Ginn et al. |
| 5,951,590 | A | 9/1999 | Goldfarb | 6,716,228 B2 | 4/2004 | Tal |
| 5,954,732 | A | 9/1999 | Hart et al. | 6,743,195 B2 | 6/2004 | Zucker |
| 5,957,936 | A | 9/1999 | Yoon et al. | 6,743,259 B2 | 6/2004 | Ginn |
| 5,957,937 | A | 9/1999 | Yoon | 6,745,079 B2 | 6/2004 | King |
| 5,957,938 | A | 9/1999 | Zhu et al. | 6,746,457 B2 | 6/2004 | Dana et al. |
| 5,964,773 | A | 10/1999 | Greenstein | 6,749,621 B2 | 6/2004 | Pantages et al. |
| 5,964,782 | A | 10/1999 | Lafontaine et al. | 6,749,622 B2 | 6/2004 | McGuckin, Jr. et al. |
| 5,972,030 | A | 10/1999 | Garrison et al. | 6,767,356 B2 | 7/2004 | Kanner et al. |
| 5,976,161 | A | 11/1999 | Kirsch et al. | 6,776,785 B1 | 8/2004 | Yencho et al. |
| 5,980,517 | A | 11/1999 | Gough et al. | 6,837,906 B2 | 1/2005 | Ginn |
| 5,980,539 | A | 11/1999 | Kontos | 6,846,319 B2 | 1/2005 | Ginn et al. |
| 5,993,466 | A | 11/1999 | Yoon | 6,890,343 B2 | 5/2005 | Ginn et al. |
| 5,993,476 | A | 11/1999 | Groiso | 6,896,692 B2 | 5/2005 | Ginn et al. |
| 5,997,555 | A | 12/1999 | Kontos | 6,911,034 B2 | 6/2005 | Nobles et al. |
| 6,001,109 | A | 12/1999 | Kontos | 6,939,357 B2 | 9/2005 | Navarro et al. |
| 6,009,877 | A | 1/2000 | Edwards | 6,964,668 B2 | 11/2005 | Modesitt et al. |
| 6,022,372 | A | 2/2000 | Kontos | 6,969,397 B2 | 11/2005 | Ginn |
| 6,024,747 | A | 2/2000 | Kontos | 7,001,400 B1 | 2/2006 | Modesitt et al. |
| 6,036,699 | A | 3/2000 | Andreas et al. | 7,029,480 B2 | 4/2006 | Klein et al. |
| 6,042,601 | A | 3/2000 | Smith | 7,029,481 B1 | 4/2006 | Burdulis, Jr. et al. |
| 6,048,351 | A | 4/2000 | Gordon et al. | 7,048,747 B2 | 5/2006 | Arcia et al. |
| 6,048,354 | A | 4/2000 | Lawrence | 7,060,084 B1 | 6/2006 | Lashakove et al. |
| 6,048,357 | A | 4/2000 | Kontos | 7,063,661 B2 | 6/2006 | Okada |
| 6,056,744 | A | 5/2000 | Edwards | 7,063,710 B2 | 6/2006 | Takamoto et al. |
| 6,068,603 | A | 5/2000 | Suzuki | 7,063,711 B1 | 6/2006 | Loshakove et al. |
| 6,077,276 | A | 6/2000 | Kontos | 7,083,635 B2 | 8/2006 | Ginn |
| 6,077,279 | A | 6/2000 | Kontos | 7,112,225 B2 | 9/2006 | Ginn |
| 6,083,242 | A | 7/2000 | Cook | 7,122,002 B2 | 10/2006 | Okada |
| 6,117,144 | A | 9/2000 | Nobles et al. | 7,147,646 B2 | 12/2006 | Dana et al. |
| 6,117,145 | A | 9/2000 | Wood et al. | 7,160,309 B2 | 1/2007 | Voss |
| 6,126,675 | A | 10/2000 | Shchervinsky et al. | 7,179,266 B2 | 2/2007 | Kontos |
| 6,132,439 | A | 10/2000 | Kontos | 7,229,458 B2 | 6/2007 | Boecker et al. |
| 6,132,440 | A | 10/2000 | Hathaway et al. | 7,235,087 B2 | 6/2007 | Modesitt et al. |
| 6,136,010 | A | 10/2000 | Modesitt et al. | 7,270,672 B1 | 9/2007 | Singer |
| 6,139,556 | A | 10/2000 | Kontos | 7,316,704 B2 | 1/2008 | Bagaoisan et al. |
| 6,143,004 | A | 11/2000 | Davis | 7,326,230 B2 | 2/2008 | Ravikumar |
| 6,152,936 | A | 11/2000 | Christy et al. | 7,331,979 B2 | 2/2008 | Khosravi et al. |
| 6,165,183 | A | 12/2000 | Kuehn et al. | 7,335,220 B2 | 2/2008 | Khosravi et al. |
| 6,165,204 | A | 12/2000 | Levinson et al. | 7,361,183 B2 | 4/2008 | Ginn |
| 6,190,396 | B1 | 2/2001 | Whitin et al. | 7,361,185 B2 | 4/2008 | O'Malley et al. |
| 6,197,042 | B1 | 3/2001 | Ginn et al. | 7,377,927 B2 | 5/2008 | Burdulis, Jr. et al. |
| 6,206,893 | B1 | 3/2001 | Klein et al. | 7,390,328 B2 | 6/2008 | Modesitt |
| 6,206,895 | B1 | 3/2001 | Levinson et al. | 7,393,363 B2 | 7/2008 | Ginn |
| 6,221,084 | B1 | 4/2001 | Fleenor | 7,431,727 B2 | 10/2008 | Cole et al. |
| 6,245,079 | B1 | 6/2001 | Nobles et al. | 7,442,198 B2 | 10/2008 | Gellman et al. |
| 6,248,124 | B1 | 6/2001 | Pedros et al. | 7,445,626 B2 | 11/2008 | Songer et al. |
| 6,296,657 | B1 | 10/2001 | Brucker | 7,449,024 B2 | 11/2008 | Stafford |
| 6,306,081 | B1 | 10/2001 | Ishikawa et al. | 7,462,188 B2 | 12/2008 | McIntosh |
| 6,322,580 | B1 | 11/2001 | Kanner | 7,507,200 B2 | 3/2009 | Okada |
| 6,348,059 | B1 | 2/2002 | Hathaway et al. | 7,727,249 B2 | 6/2010 | Rahmani |
| 6,355,050 | B1 | 3/2002 | Andreas et al. | 7,731,655 B2 | 6/2010 | Smith et al. |
| 6,358,258 | B1 | 3/2002 | Arcia et al. | 7,749,249 B2 | 7/2010 | Gelbart et al. |
| 6,395,015 | B1 | 5/2002 | Borst et al. | 7,837,696 B2 | 11/2010 | Modesitt et al. |
| 6,397,110 | B1 | 5/2002 | Kuzma | 2001/0046518 A1 | 11/2001 | Sawhney |

| Publication No. | Date | Inventor |
|---|---|---|
| 2002/0045908 A1 | 4/2002 | Nobles et al. |
| 2002/0095164 A1 | 7/2002 | Andreas et al. |
| 2002/0099389 A1 | 7/2002 | Michler et al. |
| 2002/0106409 A1 | 8/2002 | Sawhney et al. |
| 2002/0177876 A1 | 11/2002 | Roby et al. |
| 2002/0188275 A1 | 12/2002 | McGuckin et al. |
| 2003/0093093 A1 | 5/2003 | Modesitt et al. |
| 2003/0195529 A1* | 10/2003 | Takamoto et al. ............ 606/145 |
| 2003/0233095 A1 | 12/2003 | Urbanski et al. |
| 2004/0009205 A1 | 1/2004 | Sawhney |
| 2004/0092964 A1 | 5/2004 | Modesitt et al. |
| 2004/0093027 A1 | 5/2004 | Fabisiak et al. |
| 2004/0097978 A1 | 5/2004 | Modesitt et al. |
| 2004/0122449 A1 | 6/2004 | Modesitt et al. |
| 2004/0127940 A1 | 7/2004 | Ginn et al. |
| 2004/0143290 A1 | 7/2004 | Brightbill |
| 2004/0158127 A1 | 8/2004 | Okada |
| 2004/0158287 A1 | 8/2004 | Cragg et al. |
| 2004/0167511 A1 | 8/2004 | Buehlmann et al. |
| 2004/0181238 A1* | 9/2004 | Zarbatany et al. ............ 606/108 |
| 2004/0186487 A1 | 9/2004 | Klein et al. |
| 2004/0191277 A1 | 9/2004 | Sawhney et al. |
| 2004/0210251 A1* | 10/2004 | Kontos ...................... 606/224 |
| 2004/0215232 A1 | 10/2004 | Belhe et al. |
| 2004/0225301 A1 | 11/2004 | Roop et al. |
| 2004/0267193 A1 | 12/2004 | Bagaoisan et al. |
| 2004/0267308 A1 | 12/2004 | Bagaoisan et al. |
| 2005/0059982 A1 | 3/2005 | Zung et al. |
| 2005/0070923 A1 | 3/2005 | McIntosh |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0121042 A1 | 6/2005 | Belhe et al. |
| 2005/0143761 A1 | 6/2005 | Modesitt |
| 2005/0149117 A1 | 7/2005 | Khosravi et al. |
| 2005/0177189 A1 | 8/2005 | Ginn et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0273137 A1 | 12/2005 | Ginn |
| 2006/0034930 A1 | 2/2006 | Khosravi et al. |
| 2006/0047313 A1 | 3/2006 | Khanna et al. |
| 2006/0079914 A1 | 4/2006 | Modesitt et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0142785 A1 | 6/2006 | Modesitt et al. |
| 2006/0167477 A1 | 7/2006 | Arcia et al. |
| 2006/0173469 A1 | 8/2006 | Klein |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2007/0032799 A1 | 2/2007 | Pantages et al. |
| 2007/0032801 A1 | 2/2007 | Pantages et al. |
| 2007/0049967 A1 | 3/2007 | Sibbitt, Jr. et al. |
| 2007/0049968 A1 | 3/2007 | Sibbitt, Jr. et al. |
| 2007/0060895 A1 | 3/2007 | Sibbitt, Jr. et al. |
| 2007/0060950 A1 | 3/2007 | Khosravi et al. |
| 2007/0112304 A1 | 5/2007 | Voss |
| 2007/0123817 A1 | 5/2007 | Khosravi et al. |
| 2007/0167959 A1 | 7/2007 | Modesitt et al. |
| 2007/0203506 A1 | 8/2007 | Sibbitt, Jr. et al. |
| 2007/0276410 A1 | 11/2007 | McIntosh |
| 2007/0282354 A1 | 12/2007 | McIntosh |
| 2008/0009794 A1 | 1/2008 | Bagaoisan et al. |
| 2008/0045979 A1 | 2/2008 | Ma |
| 2008/0065151 A1 | 3/2008 | Ginn |
| 2008/0065152 A1 | 3/2008 | Carley |
| 2008/0287967 A1 | 11/2008 | Andreas et al. |
| 2008/0319458 A1 | 12/2008 | Reynolds |
| 2009/0005793 A1 | 1/2009 | Pantages et al. |
| 2009/0036906 A1 | 2/2009 | Stafford |
| 2009/0048615 A1 | 2/2009 | McIntosh |
| 2009/0088779 A1 | 4/2009 | Zung et al. |
| 2009/0157105 A1 | 6/2009 | Zung et al. |
| 2009/0254119 A1 | 10/2009 | Sibbitt, Jr. et al. |
| 2010/0130965 A1 | 5/2010 | Sibbitt, Jr. et al. |

FOREIGN PATENT DOCUMENTS

| | | |
|---|---|---|
| DE | 4210724 | 7/1993 |
| DE | 9217932 | 7/1993 |
| DE | 4220283 | 12/1993 |
| DE | 10211360 | 10/2003 |
| EP | 0 140 557 | 5/1985 |
| EP | 0 207 545 | 1/1987 |
| EP | 0 474 887 | 3/1992 |
| EP | 0 478 358 | 4/1992 |
| EP | 0 478 887 | 4/1992 |
| EP | 0 543 499 | 10/1992 |
| EP | 0 542 126 | 5/1993 |
| EP | 0 568 098 | 11/1993 |
| EP | 0 589 409 | 3/1994 |
| EP | 0 624 343 | 11/1994 |
| EP | 0 669 101 | 8/1995 |
| EP | 0 669 102 | 8/1995 |
| EP | 0 669 103 | 8/1995 |
| EP | 0 684 012 | 11/1995 |
| EP | 0 812 571 | 12/1997 |
| EP | 0 941 698 | 9/1999 |
| FR | 1059544 | 3/1954 |
| FR | 2768324 | 3/1999 |
| JP | 51143386 | 11/1976 |
| JP | 5220794 | 2/1977 |
| JP | 2119866 | 5/1990 |
| JP | 542161 | 2/1993 |
| SU | 820810 | 4/1981 |
| SU | 993922 | 2/1983 |
| SU | 1093329 | 5/1984 |
| SU | 1174036 | 8/1985 |
| SU | 1544383 | 2/1990 |
| SU | 1648400 | 5/1991 |
| WO | WO 85/03858 | 9/1985 |
| WO | WO 94/05213 | 3/1994 |
| WO | WO 94/13211 | 6/1994 |
| WO | WO 94/27503 | 12/1994 |
| WO | WO 94/28801 | 12/1994 |
| WO | WO 95/05121 | 2/1995 |
| WO | WO 95/13021 | 5/1995 |
| WO | WO 95/25468 | 9/1995 |
| WO | WO 95/35065 | 12/1995 |
| WO | WO 96/09006 | 3/1996 |
| WO | WO 97/00046 | 1/1997 |
| WO | WO 97/03613 | 2/1997 |
| WO | WO 97/07745 | 3/1997 |
| WO | WO 97/10764 | 3/1997 |
| WO | WO 97/13461 | 4/1997 |
| WO | WO 97/17901 | 5/1997 |
| WO | WO 97/20505 | 6/1997 |
| WO | WO 97/27897 | 8/1997 |
| WO | WO 98/04195 | 2/1998 |
| WO | WO 98/42262 | 10/1998 |
| WO | WO 99/47049 | 9/1999 |
| WO | WO 00/12013 | 3/2000 |
| WO | WO 00/51498 | 9/2000 |
| WO | WO 00/69342 | 11/2000 |
| WO | WO 01/19259 | 3/2001 |
| WO | WO 01/35833 | 5/2001 |
| WO | WO 02/36021 | 5/2002 |
| WO | WO 02/062234 | 8/2002 |
| WO | WO 03/003925 | 1/2003 |
| WO | WO 03/094748 | 11/2003 |
| WO | WO 03/099134 | 12/2003 |
| WO | WO 2005/000126 | 1/2005 |
| WO | WO 2005/023119 | 3/2005 |
| WO | WO 2005/025430 | 3/2005 |
| WO | WO 2005/030060 | 4/2005 |
| WO | WO 2005/041782 | 5/2005 |
| WO | WO 2005/063129 | 7/2005 |
| WO | WO 2005/065549 | 7/2005 |
| WO | WO 2005/092204 | 10/2005 |
| WO | WO 2005/112782 | 12/2005 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/115901 | 11/2006 |
| WO | WO 2006/115904 | 11/2006 |

| | | |
|---|---|---|
| WO | WO 2006/118877 | 11/2006 |
| WO | WO 2007/019016 | 2/2007 |
| WO | WO 2007/025014 | 3/2007 |
| WO | WO 2007/025017 | 3/2007 |
| WO | WO 2007/025018 | 3/2007 |
| WO | WO 2007/025019 | 3/2007 |
| WO | WO 2007/081836 | 7/2007 |
| WO | WO 2010/031050 | 3/2010 |

OTHER PUBLICATIONS

U.S. Appl. No. 11/199,338, Mail Date Jan. 6, 2009, Office Action.
U.S. Appl. No. 11/199,515, Mail Date Aug. 20, 2008, Office Action.
U.S. Appl. No. 11/199,515, Mail Date Nov. 13, 2008, Office Action.
2007/0032801, Office Action, Mail Date Jan. 25, 2007.
2007/0032801, Office Action, Mail Date Oct. 5, 2007.
U.S. Appl. No. 10/948,445, filed Sep. 22, 2004, McIntosh.
U.S. Appl. No. 12/257,127, Mail Date Dec. 22, 2010, Office Action.
U.S. Appl. No. 12/334,085, Mail Date Dec. 23, 2010, Office Action.
U.S. Appl. No. 11/508,656, Mail Date Aug. 30, 2010, Office Action.
U.S. Appl. No. 60/506,536, filed Sep. 26, 2003, McIntosh.
U.S. Appl. No. 60/540,811, filed Jan. 30, 2004, McIntosh.
U.S. Appl. No. 60/711,279, filed Aug. 24, 2005, Sibbitt, Jr. et al.
U.S. Appl. No. 60/726,985, filed Oct. 14, 2005, Sibbitt, Jr. et al.
U.S. Appl. No. 61/097,072, filed Sep. 15, 2008, Sibbitt, Jr. et al.
U.S. Appl. No. 90/006,469, filed Nov. 29, 2002, Modesitt et al.
US 5,820,544, Semm, (withdrawn).
Cardiac Catheterization and Angiography, 3rd Ed., Lea N ad Febiger, Philadelphia, 1986. Elgiloy Brochure, Jun. 23, 1959, Elgin National Watch Co., Elgin, IL.
Cardio-Thoracic Systems Prospectus dated Mar. 20, 1996.
Datascope Corporation, Montvale, NJ (1991) 1 PG, American Heart Assoc. Meeting, Anaheim.
Elgiloy Brochure, Jun. 23, 1959, Elgin National Watch Co., Elgin, IL.
Kensey Nash Corporation, Exton, PA, "The Hemostatic Puncture Closure Device", 2 pages.
Laurus Medical Corporation, "Endoscopic Suturing Made Simple," The Laurus ND-2600 Needle Driver, Irvine, CA., 1 page.
Marshall, A.C. & Lock, J.E.; "Structural and compliant anatomy of the patient foramen ovale in patients undergoing transcatheter closure", Am. Heart Journ., 140(2):303-307 (2000).
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc.
Product Brochure, Laurus Medical Corporation, Irvine, CA "The Laurus In-Line Endoscopic Suturing Device" (Oct. 1994) 1 page.
Rema-Medizintcchnik GmbH, Product Brochure entitled "REMA," 7 pages.
Serruys, PW et al., A Comparision of Balloon-Expandable-Stent Implantaion With Balloon Angioplastiy in Patients With Coronary Artery Disease, New England Journal of Medicine, 331:489-495, 1994.
Taber's Cyclopedic Medical Dictionary, 18th Ed., p. 747 (1997).
U.S. Appl. No. 07/989,611, Mail Date May 12, 1993, Office Action.
U.S. Appl. No. 07/989,611, Mail Date Aug. 1, 1994, Office Action.
U.S. Appl. No. 07/989,611, Mail Date Nov. 3, 1994, Notice of Allowance.
U.S. Appl. No. 08/148,809, Mail Date Sep. 16, 1994, Office Action.
U.S. Appl. No. 08/148,809, Mail Date May 30, 1995, Office Action.
U.S. Appl. No. 08/148,809, Mail Date Oct. 26, 1995, Office Action.
U.S. Appl. No. 08/148,809, Mail Date Dec. 15, 1995, Notice of Allowance.
U.S. Appl. No. 08/252,124, Mail Date Jun. 5, 1995, Office Action.
U.S. Appl. No. 08/252,124, Mail Date Jan. 5, 1996, Office Action.
U.S. Appl. No. 08/252,124, Mail Date May 22, 1996, Notice of Allowance.
U.S. Appl. No. 08/259,410, Mail Date Feb. 2, 1995, Office Action.
U.S. Appl. No. 08/259,410, Mail Date Jun. 1, 1995, Office Action.
U.S. Appl. No. 08/259,410, Mail Date Feb. 6, 1998, Notice of Allowance.
U.S. Appl. No. 08/638,076, Mail Date Jan. 21, 1997, Office Action.
U.S. Appl. No. 08/638,076, Mail Date Oct. 17, 1997, Notice of Allowance.
U.S. Appl. No. 08/824,031, Mail Date Mar. 16, 1998, Office Action.
U.S. Appl. No. 08/824,031, Mail Date Sep. 14, 1998, Office Action.
U.S. Appl. No. 08/824,031, Mail Date Apr. 13, 1999, Office Action.
U.S. Appl. No. 08/824,031, Mail Date Jul. 15, 1999, Notice of Allowance.
U.S. Appl. No. 08/883,246, Mail Date Jul. 23, 1998, Office Action.
U.S. Appl. No. 08/883,246, Mail Date Apr. 12, 1999, Office Action.
U.S. Appl. No. 08/883,246, Mail Date Oct. 13, 1999, Office Action.
U.S. Appl. No. 08/883,246, Mail Date Oct. 23, 2000, Office Action.
U.S. Appl. No. 08/883,246, Mail Date Jul. 11, 2001, Office Action.
U.S. Appl. No. 08/883,246, Mail Date Sep. 11, 2001, Notice of Allowance.
U.S. Appl. No. 09/057,108, Mail Date Jul. 10, 2000, Office Action.
U.S. Appl. No. 09/057,108, Mail Date Oct. 25, 2000, Notice of Allowance.
U.S. Appl. No. 09/262,402, Mail Date Mar. 29, 2000, Office Action.
U.S. Appl. No. 09/262,402, Mail Date May 30, 2000, Notice of Allowance.
U.S. Appl. No. 09/395,901, Mail Date Jun. 27, 2000, Office Action.
U.S. Appl. No. 09/395,901, Mail Date Nov. 6, 2000, Office Action.
U.S. Appl. No. 09/395,901, Mail Date Apr. 20, 2001, Notice of Allowance.
U.S. Appl. No. 09/395,901, Mail Date Sep. 10, 2001, Notice of Allowance.
U.S. Appl. No. 09/610,099, Mail Date Jul. 11, 2002, Office Action.
U.S. Appl. No. 09/610,099, Mail Date Dec. 24, 2002, Notice of Allowance.
U.S. Appl. No. 09/651,344, Mail DateFeb. 28, 2003, Office Action.
U.S. Appl. No. 09/651,344, Mail Date Nov. 7, 2003, Office Action.
U.S. Appl. No. 09/651,344, Mail Date Apr. 20, 2004, Notice of Allowance.
U.S. Appl. No. 09/707,746, Mail Date Feb. 16, 2005, Office Action.
U.S. Appl. No. 09/707,746, Mail Date Jul. 7, 2005, Office Action.
U.S. Appl. No. 09/707,746, Mail Date Nov. 15, 2005, Notice of Allowance.
U.S. Appl. No. 09/769,109, Mail Date Oct. 23, 2001, Office Action.
U.S. Appl. No. 09/769,109, Mail Date Jun. 17, 2002, Office Action.
U.S. Appl. No. 09/769,109, Mail Date Sep. 9, 2002, Notice of Allowance.
U.S. Appl. No. 09/988,541, Mail Date Mar. 17, 2004, Office Action.
U.S. Appl. No. 09/988,541, Mail Date Feb. 28, 2005, Office Action.
U.S. Appl. No. 09/988,541, Mail Date May 25, 2005, Office Action.
U.S. Appl. No. 09/988,541, Mail Date Aug. 24, 2005, Office Action.
U.S. Appl. No. 09/988,541, Mail Date Nov. 8, 2005, Office Action.
U.S. Appl. No. 09/988,541, Mail Date Dec. 13, 2005, Notice of Allowance.
U.S. Appl. No. 10/033,689, Mail Date Sep. 30, 2003, Office Action.
U.S. Appl. No. 10/152,272, Mail Date Jan. 24, 2005, Office Action.
U.S. Appl. No. 10/152,272, Mail Date May 13, 2005, Notice of Allowance.
U.S. Appl. No. 10/335,065, Mail Date Mar. 17, 2005, Office Action.
U.S. Appl. No. 10/335,065, Mail Date Jun. 10, 2005, Office Action.
U.S. Appl. No. 10/335,065, Mail Date Nov. 17, 2005, Notice of Allowance.
U.S. Appl. No. 10/335,147, Mail Date Dec. 13, 2005, Office Action.
U.S. Appl. No. 10/335,147, Mail Date Apr. 17, 2006, Office Action.
U.S. Appl. No. 10/335,147, Mail Date Oct. 4, 2006, Notice of Allowance.
U.S. Appl. No. 10/357,984, Mail Date Jan. 9, 2006, Office Action.
U.S. Appl. No. 10/357,984, Mail Date Mar. 16, 2006, Office Action.
U.S. Appl. No. 10/357,984, Mail Date Sep. 28, 2006, Office Action.
U.S. Appl. No. 10/357,984, Mail Date Mar. 23, 2007, Office Action.
U.S. Appl. No. 10/357,984, Mail Date Nov. 14, 2007, Office Action.
U.S. Appl. No. 10/652,182, Mail Date Aug. 9, 2006, Office Action.
U.S. Appl. No. 10/652,182, Mail Date Feb. 22, 2007, Notice of Allowance.
U.S. Appl. No. 10/660,288, Mail Date Nov. 15, 2005, Office Action.
U.S. Appl. No. 10/660,288, Mail Date Mar. 9, 2006, Office Action.
U.S. Appl. No. 10/660,288, Mail Date Aug. 24, 2006, Office Action.
U.S. Appl. No. 10/660,288, Mail Date Feb. 1, 2007, Office Action.
U.S. Appl. No. 10/660,288, Mail Date Jun. 28, 2007, Office Action.

U.S. Appl. No. 10/660,288, Mail Date Apr. 29, 2009, Office Action.
U.S. Appl. No. 10/660,288, Mail Date Aug. 3, 2009, Office Action.
U.S. Appl. No. 10/660,288, Mail Date Mar. 30, 2010, Office Action.
U.S. Appl. No. 10/729,541, Mail Date Dec. 12, 2006, Office Action.
U.S. Appl. No. 10/729,541, Mail Date Jun. 18, 2007, Office Action.
U.S. Appl. No. 10/729,541, Mail Date Jan. 8, 2008, Office Action.
U.S. Appl. No. 10/729,541, Mail Date Sep. 23, 2008, Office Action.
U.S. Appl. No. 10/729,541, Mail Date May 1, 2009, Office Action.
U.S. Appl. No. 10/729,541, Mail Date Nov. 16, 2009, Notice of Allowance.
U.S. Appl. No. 10/729,541, Mail Date Mar. 25, 2010, Notice of Allowance.
U.S. Appl. No. 10/729,541, Mail Date Jul. 12, 2010, Notice of Allowance.
U.S. Appl. No. 10/737,668, Mail Date Nov. 2, 2005, Office Action.
U.S. Appl. No. 10/737,668, Mail Date Feb. 16, 2006, Office Action.
U.S. Appl. No. 10/737,668, Mail Date Oct. 19, 2006, Office Action.
U.S. Appl. No. 10/737,668, Mail Date Jun. 7, 2007, Office Action.
U.S. Appl. No. 10/737,668, Mail Date Nov. 28, 2007, Office Action.
U.S. Appl. No. 10/737,668, Mail Date Jun. 26, 2008, Notice of Allowance.
U.S. Appl. No. 10/742,406, Mail Date Mar. 23, 2007, Office Action.
U.S. Appl. No. 10/742,406, Mail Date Sep. 10, 2007, Notice of Allowance.
U.S. Appl. No. 10/742,406, Mail Date Jan. 11, 2008, Notice of Allowance.
U.S. Appl. No. 10/813,449, Mail Date Sep. 5, 2006, Office Action.
U.S. Appl. No. 10/813,449, Mail Date Jul. 16, 2007, Office Action.
U.S. Appl. No. 10/813,449, Mail Date Jan. 25, 2008, Office Action.
U.S. Appl. No. 10/813,449, Mail Date Aug. 14, 2008, Office Action.
U.S. Appl. No. 10/813,449, Mail Date Sep. 15, 2008, Office Action.
U.S. Appl. No. 10/813,449, Mail Date Feb. 3, 2009, Office Action.
U.S. Appl. No. 10/813,449, Mail Date Aug. 28, 2009, Office Action.
U.S. Appl. No. 10/813,449, Mail Date May 27, 2010, Office Action.
U.S. Appl. No. 10/909,531, Mail Date Apr. 4, 2007, Office Action.
U.S. Appl. No. 10/909,531, Mail Date Dec. 26, 2007, Office Action.
U.S. Appl. No. 10/909,531, Mail Date Jun. 13, 2008, Office Action.
U.S. Appl. No. 10/909,531, Mail Date Feb. 9, 2009, Office Action.
U.S. Appl. No. 10/909,531, Mail Date Sep. 16, 2009, Office Action.
U.S. Appl. No. 10/909,531, Mail Date Apr. 29, 2010, Notice of Allowance.
U.S. Appl. No. 10/948,445, Mail Date Jul. 11, 2007, Office Action.
U.S. Appl. No. 11/199,515, Mail Date Jun. 10, 2009, Office Action.
U.S. Appl. No. 11/199,515, Mail Date Dec. 24, 2009, Notice of Allowance.
U.S. Appl. No. 11/199,515, Mail Date Apr. 2, 2010, Notice of Allowance.
U.S. Appl. No. 11/273,107, Mail Date Jun. 14, 2007, Office Action.
U.S. Appl. No. 11/273,107, Mail Date Jan. 18, 2008, Office Action.
U.S. Appl. No. 11/273,107, Mail Date Sep. 5, 2008, Office Action.
U.S. Appl. No. 11/273,107, Mail Date Apr. 9, 2009, Office Action.
U.S. Appl. No. 11/273,107, Mail Date Oct. 28, 2009, Office Action.
U.S. Appl. No. 11/273,107, Mail Date Jun. 2, 2010, Office Action.
U.S. Appl. No. 11/316,775, Mail Date Apr. 16, 2008, Office Action.
U.S. Appl. No. 11/316,775, Mail Date Aug. 6, 2008, Office Action.
U.S. Appl. No. 11/363,005, Mail Date Jun. 22, 2007, Office Action.
U.S. Appl. No. 11/363,005, Mail Date Dec. 14, 2007, Office Action.
U.S. Appl. No. 11/363,005, Mail Date Apr. 17, 2008, Office Action.
U.S. Appl. No. 11/363,005, Mail Date Dec. 23, 2008, Office Action.
U.S. Appl. No. 11/363,005, Mail Date Jul. 10, 2009, Notice of Allowance.
U.S. Appl. No. 11/363,005, Mail Date Jan. 14, 2010, Notice of Allowance.
U.S. Appl. No. 11/389,762, Mail Date Sep. 20, 2007, Notice of Allowance.
U.S. Appl. No. 11/389,762, Mail Date Nov. 23, 2007, Notice of Allowance.
U.S. Appl. No. 11/390,937, Mail Date Sep. 7, 2007, Office Action.
U.S. Appl. No. 11/391,951, Mail Date Oct. 28, 2008, Office Action.
U.S. Appl. No. 11/391,951, Mail Date Jan. 30, 2009 Office Action.
U.S. Appl. No. 11/391,951, Mail Date Aug. 26, 2009 Office Action.
U.S. Appl. No. 11/391,951, Mail Date Jun. 23, 2010 Office Action.
U.S. Appl. No. 11/465,527, Mail Date Feb. 3, 2010 Office Action.

U.S. Appl. No. 11/508,656, Mail Date Dec. 9, 2009, Office Action.
U.S. Appl. No. 11/508,656, Mail Date Mar. 25, 2010, Office Action.
U.S. Appl. No. 11/508,662, Mail Date Dec. 28, 2009, Office Action.
U.S. Appl. No. 11/508,662, Mail Date Apr. 14, 2010, Office Action.
U.S. Appl. No. 11/508,715, Mail Date Jan. 6, 2010, Office Action.
U.S. Appl. No. 11/508,715, Mail Date Apr. 26, 2010, Office Action.
U.S. Appl. No. 11/552,593, Mail Date Aug. 21, 2008, Office Action.
U.S. Appl. No. 11/552,593, Mail Date Feb. 5, 2009, Office Action.
U.S. Appl. No. 11/552,593, Mail Date Oct. 13, 2009, Notice of Allowance.
U.S. Appl. No. 11/552,593, Mail Date Mar. 22, 2010, Notice of Allowance.
U.S. Appl. No. 11/688,722, Mail Date Mar. 10, 2010, Office Action.
U.S. Appl. No. 11/891,358, Mail Date Apr. 26, 2010, Office Action.
U.S. Appl. No. 11/891,513, Mail Date Apr. 9, 2010, Office Action.
U.S. Appl. No. 90/006,469, Mail Date Nov. 29, 2002, Request for Re-Examination.
U.S. Appl. No. 90/006,469, Mail Date Sep. 10, 2004, Re-Examination Office Action.
U.S. Appl. No. 90/006,469, Mail Date Sep. 27, 2005, Notice of Intent.
U.S. Appl. No. 90/006,469, Mail Date Jun. 27, 2006, Re-Examination Certification.
U.S. Appl. No. 12/966,961, filed Dec. 13, 2010, Modesitt, et al.
U.S. Appl. No. 10/909,531, Mail Date Nov. 23, 2010, Issue Notification.
U.S. Appl. No. 11/363,005, Mail Date Nov. 10, 2010, Issue Notification.
U.S. Appl. No. 11/465,527, Mail Date Nov. 10, 2010, Issue Notification.
U.S. Appl. No. 11/552,593, Mail Date Nov. 10, 2010, Issue Notification.
U.S. Appl. No. 11/688,722, Mail Date Nov. 17, 2010, Issue Notification.
U.S. Appl. No. 12/182,836, Mail Date Oct. 5, 2010, Office Action.
U.S. Appl. No. 10/729,541, Mail Date Nov. 23, 2010, Issue Notification.
U.S. Appl. No. 11/273,107, Mail Date Oct. 27, 2010, Office Action.
U.S. Appl. No. 11/508,662, Mail Date Oct. 26, 2010, Office Action.
U.S. Appl. No. 11/960,593, Mail Date Nov. 3, 2010, Office Action.
U.S. Appl. No. 12/334,077, Mail Date Oct. 27, 2010, Office Action.
U.S. Appl. No. 11/891,513, Mail Date Sep. 28, 2010, Office Action.
U.S. Appl. No. 12/365,397, Mail Date Sep. 13, 2010, Office Action.
U.S. Appl. No. 60/946,063, filed Jun. 25, 2007, Reynolds.
U.S. Appl. No. 10/746,210, Mail Date Apr. 5, 2007, Office Action.
U.S. Appl. No. 10/746,210, Mail Date Aug. 21, 2007, Office Action.
U.S. Appl. No. 10/746,210, Mail Date Jul. 9, 2008, Notice of Allowance.
U.S. Appl. No. 10/877,974, Mail Date Jul. 9, 2008, Office Action.
U.S. Appl. No. 10/909,531, Mail Date Aug. 20, 2010, Notice of Allowance.
U.S. Appl. No. 11/199,515, Mail Date Aug. 2, 2010, Notice of Allowance.
U.S. Appl. No. 11/363,005, Mail Date Jul. 23, 2010, Notice of Allowance.
U.S. Appl. No. 11/465,527, Mail Date Jul. 23, 2010, Notice of Allowance.
U.S. Appl. No. 11/688,722, Mail Date Jul. 29, 2010, Notice of Allowance.
U.S. Appl. No. 12/257,127, Mail Date Aug. 30, 2010, Office Action.
U.S. Appl. No. 12/950,338, filed Nov. 19, 2010, Modesitt, et al.
U.S. Appl. No. 12/955,848, filed Nov. 29, 2010, Modesitt, et al.
U.S. Appl. No. 12/955,863, filed Nov. 29, 2010, Dawn Ma.
U.S. Appl. No. 12/955,869, filed Nov. 29, 2010, Voss.
U.S. Appl. No. 11/508,715, Mail Date Oct. 18, 2010, Office Action.
U.S. Appl. No. 11/891,358, Mail Date Oct. 19, 2010, Office Action.
U.S. Appl. No. 11/960,593, Mail Date Sep. 14, 2010, Office Action.
U.S. Appl. No. 12/182,836, Mail Date Oct. 5, 2010, Office Action.
U.S. Appl. No. 12/961,239, filed Dec. 6, 2010, Modesitt, et al.
U.S. Appl. No. 11/552,593, Mail Date Jul. 22, 2010, Notice of Allowance.
U.S. Appl. No. 11/199,515, Mail Date Jan. 19, 2011, Issue Notification.

U.S. Appl. No. 11/273,107, Mail Date Jun. 2, 2011, Notice of Allowance.
U.S. Appl. No. 11/960,593, Mail Date Apr. 28, 2011, Office Action.
U.S. Appl. No. 12/950,338, Mail Date Jun. 15, 2011, Office Action.
U.S. Appl. No. 12/182,836, Mail Date Jun. 23, 2011, Office Action.
U.S. Appl. No. 12/257,127, Mail Date Jul. 6, 2011, Office Action.
U.S. Appl. No. 12/955,848, Mail Date Jun. 30, 2011, Office Action.
U.S. Appl. No. 11/997,379, Mail Date Jul. 13, 2001, Office Action.
U.S. Appl. No. 13/022,050, Mail Date Jul. 11, 2001, Office Action.
U.S. Appl. No. 12/334,077, Mail Date Jul. 21, 2011, Office Action.
U.S. Appl. No. 12/961,239, Mail Date Jul. 26, 2011, Notice of Allowance.
U.S. Appl. No. 12/334,085, Mail Date Aug. 4, 2011, Office Action.
U.S. Appl. No. 10/660,288, Mail Date Mar. 29, 2011, Office Action.
U.S. Appl. No. 11/199,515, Mail Date Jan. 19, 2011, Issue Notification.
U.S. Appl. No. 12/966,961, filed Aug. 18, 2011, Notice of Allowance.
U.S. Appl. No. 10/660,288, filed Sep. 30, 2011, Notice of Allowance.
U.S. Appl. No. 11/273,107 Sep. 28, 2011, Issue Notification.
U.S. Appl. No. 11/891,358, filed Aug. 31, 2011, Notice of Allowance.
U.S. Appl. No. 11/891,513, filed Aug. 31, 2011, Notice of Allowance.
U.S. Appl. No. 12/247,012, filed Oct. 13, 2011 Office Action.
U.S. Appl. No. 12/961,239, filed Oct. 12, 2011 Issue Notification.
U.S. Appl. No. 12/955,869, filed Oct. 18, 2011, Office Action.
U.S. Appl. No. 11/891,513, filed Nov. 1, 2011, Notice of Allowance.
U.S. Appl. No. 12/950,338, filed Nov. 1, 2011, Notice of Allowance.
U.S. Appl. No. 12/966,961, filed Oct. 26, 2011, Issue Notification.

* cited by examiner

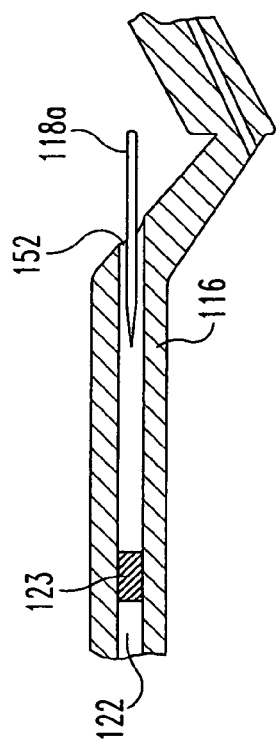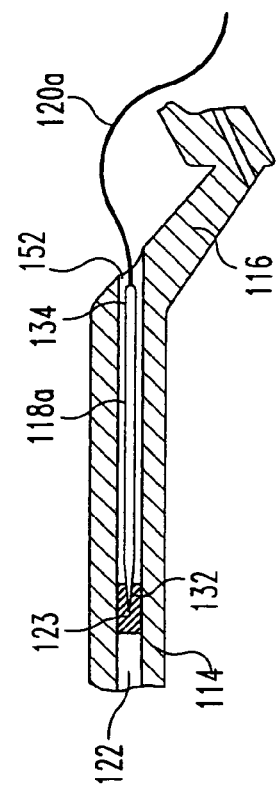

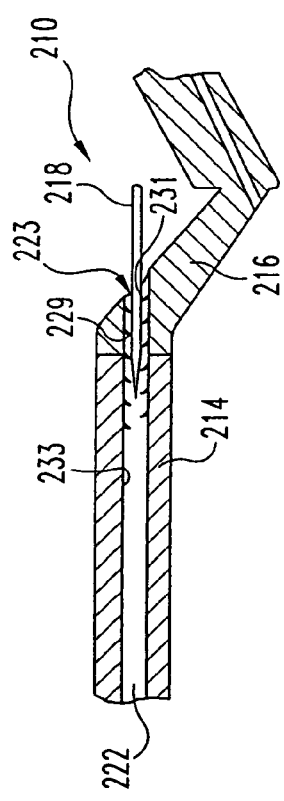
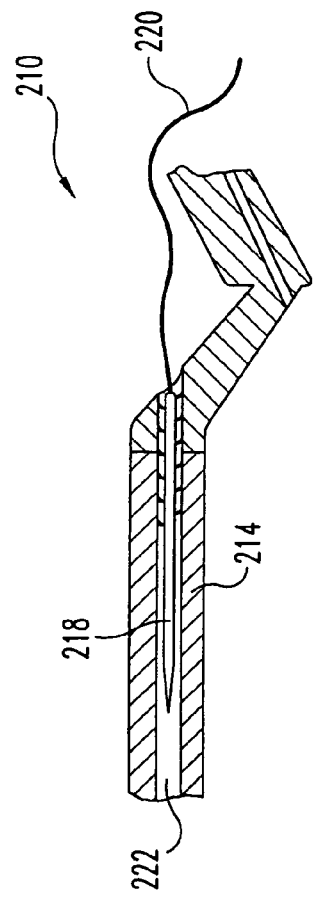

VASCULAR SUTURING DEVICE WITH NEEDLE CAPTURE

BACKGROUND OF THE INVENTION

The present invention generally relates to surgical instruments and methods of suturing tissue.

A number of diagnostic and treatment procedures are conducted intravascularly. Typically, a catheter is introduced into the vascular system at a convenient access location and is then guided to the target treatment site. The Seldinger Technique is one of the well-known early examples of this type of procedure which can include catheterization and angioplasty techniques. Procedures such as this require a vascular access. Typically an introducer sheath with or without a guide wire is inserted through a puncture wound in a vessel such as the femoral artery at a location near the groin. A catheter and other instrumentation can then be inserted through the sheath and guided to the targeted treatment site. After the diagnostic and/or treatment procedure has been completed, the puncture wound must be closed. Closing the wound can be difficult because of the substantial bleeding that can occur through an open wound in the vascular vessel. One technique for hemostasis includes applying pressure near or upstream of the puncture site. This approach suffers from many deleterious effects, not the least of which are that it can be time consuming and extremely uncomfortable—even painful—for the patient because the pressure is applied directly on or adjacent to the traumatized site. Frequently anticoagulants are employed for the original diagnostic/treatment procedures. This delays clot formation during the procedure, and this effect lasts through the initial recovery period, lengthening the time during which pressure must be applied to the wound for up to twelve hours or more. During this initial recovery period, it is imperative that the patient remain still, further adding to the patient's discomfort.

Alternatively, the puncture wound can be closed with sutures. This can be extremely difficult because the vascular vessel with the puncture lies underneath the patient's outer skin. Some vascular vessels, notably the femoral artery, appear to be relatively large; however, in practice, even the largest arteries cannot be readily sutured. Therefore, devices have been developed to facilitate subcutaneous suturing of arteries and veins. These devices can extend through the outer tissue to the puncture wound in the vascular vessel. Needles are then deployed from the device to suture the tissue adjacent the puncture wound.

Certain devices are inserted through the wound and initially deploy a needle to pierce the tissue in from outside the vascular vessel and continue on into a receptacle in the portion of the device located within the lumen of the vessel. The suturing device can be removed from the vessel (and the patient) by withdrawing the needles and suture material at the same time. However, under certain conditions the needles may not be fully captured within the depository or the needles can become dislodged upon removal of the device from the patient. This can be particularly prone to occur when the needles remain attached to the suture material. For example, as the device (with the suture attached to needles) is withdrawn, friction from drawing the suture material through tissue tends to pull the needles out of the depository. In any event, the dislodged needles catch on tissue. This can result in snagging and possibly tearing of the vascular tissue or the upper tissue layers depending upon when the needles become dislodged.

In view of the above background, there remain needs for improved and/or alternative methods and devices for closing vascular opening or punctures. The present invention is addressed to these needs.

SUMMARY OF THE INVENTION

The present invention relates to a suturing device and the use thereof. Various aspects of the invention are novel, non-obvious, and provide various advantages. While the actual nature of the invention covered herein can only be determined with reference to the claims appended hereto, certain forms and features, which are characteristic of the preferred embodiments disclosed herein, are described briefly as follows.

In one form, the present invention provides a suturing device for suturing. The suturing device provides particular advantages, for suturing a wall portion of a vascular vessel. The device comprises: a proximal member including an elongate body with a channel sized to receive a needle therein; a distal member comprising a receptacle therein, where the distal member is configured to be inserted into a vascular vessel, and wherein the receptacle is sized to receive at least one needle therein; an intermediate member disposed between the proximal member and distal member, where the intermediate member defines a tissue receiving area and provides a first passageway from the channel to the tissue receiving area and second passageway from the receptacle in the distal member to the tissue receiving area. In preferred embodiments a needle capture element positioned in the receptacle of the distal member. The needle capture element is configured to secure a needle inserted into the receptacle.

In another form, the present invention provides a method of suturing vascular tissue adjacent an opening in a vascular vessel. The method uses a suturing device which can be inserted through the opening in the vascular vessel. The device comprises: a proximal member with a needle channel formed therein; a distal member configured to be inserted into the lumen of the vascular vessel, where the distal member has a receptacle that includes a needle capture element and which is sized to receive at least one needle; and an intermediate member disposed between the proximal member and the distal member. The intermediate member defines a tissue receiving area and is configured to provide a linear needle pathway between the channel and the receptacle. A needle is advanced through or along the needle channel to pierce the vascular tissue drawing a portion of the length of suture material through the vascular tissue. The needle is further advanced so that a portion of the needle engages with the needle capture element in the receptacle. Preferable the needle capture element prevents and in adverting dislodging of the needle from the receptacle during the surgical procedure. However, the same needle capture element also allows the surgeon to remove the needle when and if desired.

BRIEF DESCRIPTION OF THE DRAWINGS

FIG. 2 is an enlarged view in cross section of the distal member of the suturing device of FIG. 1.

FIG. 3 is an enlarged view in cross section of the distal member of the suturing device of FIG. 1 with a needle disposed within a receptacle in the distal member.

FIG. 4 is an enlarged view in cross section of an intermediate member with needle engaging projections of an alternative suturing device in accordance with the present invention.

FIG. 5 is an enlarged view in cross section of the distal member illustrated in FIG. 4 with a needle disposed in the receptacle.

DETAILED DESCRIPTION OF THE INVENTION

Figure 1:
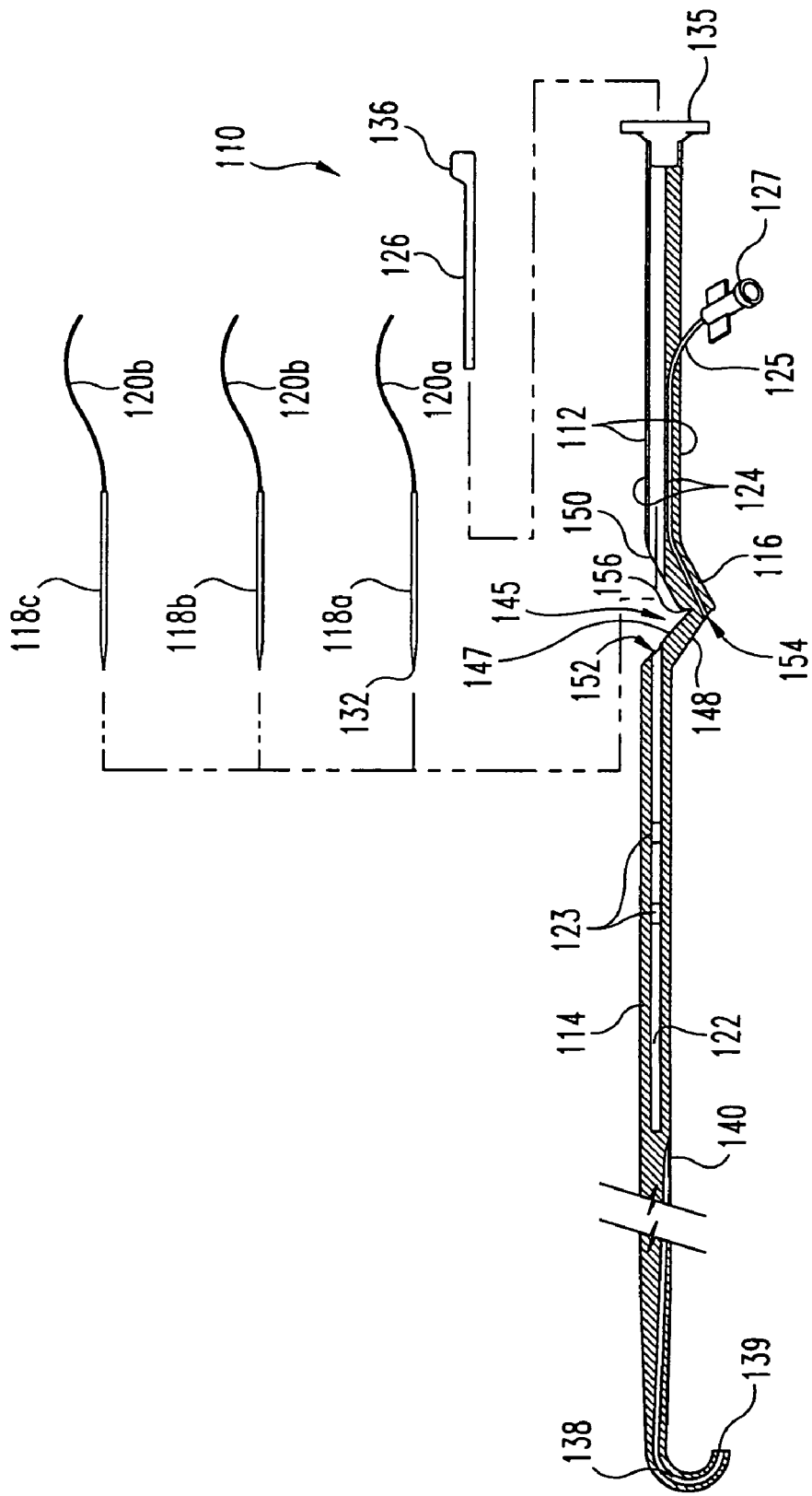
FIG. 1 is a cross-sectional view of one embodiment of a suturing device with a needle capture element in accordance with the present invention.

FIG. 1 shows a suturing device 110 for suturing vascular vessels in accordance with the present invention. Device 110 includes a proximal member 112, a distal member 114, and an intermediate member 116 located therebetween. Device 110 includes one or more needles 118a, 118b, 118c . . . disposable within needle channel 124 of proximal member 112. Each of needles 118a, 118b, 118c . . . can include a length of suture material 120a, 120b, 120c . . . secured to the proximal end of the needles. Needle pusher 126 can be used to advance the needles 118a, 118b, 118c, . . . through channel 124 out through first opening 150 into a tissue receiving area 145 defined by intermediate member 116. Preferably, proximal member 112 and/or distal member 114 define a longitudinal axis and (either/both) is/are essentially linear about this axis. In one embodiment, the intermediate member 116 can be configured to deviate from the linearity defined by either the proximal member (or the distal member). First opening 150 and second opening 152 in intermediate member can be axially aligned to permit needles 118a, 118b, 118c . . . to travel in an essentially linear needle path that extends through tissue received within tissue receiving area 145. In one form, suture material can be attached to the needle 118a. The needle is then advanced in a distal direction through tissue. A second needle 118b (and subsequent needles) can be similarly configured and manipulated to place sutures about tissue adjacent a puncture wound in a vascular vessel. The suture material(s) threaded through the vascular tissue can be drawn taut closing the puncture wound. A surgical knot or other suture securing device can complete the wound closure.

As used herein, the term "proximal" refers to a direction toward the surgeon and away from the patient or a location closer to the surgeon, while the term "distal" refers to a direction towards the patient and away from the surgeon or a location closer to the patient.

Proximal member 112 is provided as an elongated portion and can exhibit a substantially cylindrical or oval radial cross section. Member 112 includes a first end of sufficient dimensions to be readily grasped by the surgeon to manipulate the device during the procedures. Proximal member 112 can also include a gripping portion 135 to facilitate handling during the surgical procedure. Needle channel 124 runs longitudinally along at least a portion of proximal member 112. In one embodiment, channel 124 extends along the entire length of proximal member from a first end positioned proximal to the surgeon to a second end adjacent to intermediate member 116. In this embodiment, one or more needle(s) 118a, 118b, 118c, . . . and a needle pusher 126 and grip 136 can be inserted into and retrieved from channel 124 at the first end. In other embodiments, channel 124 extends only partly through the proximal member 112. Needle channel 124 can be centrally located along proximal member 112. In preferred embodiments, proximal member 112 includes a single needle channel 124 through which one, two, three, or more needles can be advanced. Alleviating multiple needle channels within the suturing device provides a more compact member, which can be particularly advantageous for subcutaneous procedures.

Channel 124 is sized and dimensioned to allow one or more needles 118a, 118b, 118c . . . to be advanceable therethrough and into vascular tissue around the puncture wound. Furthermore, channel 124 can be either partly or completely encased within the body of proximal member 112. However, in a preferred embodiment, channel 124 is not encased within the body of proximal member 112. Rather, channel 124 is provided as a slot formed into the surface of proximal member 112. Preferably the slot is configured to retain one or more needles within the slot. For example, the slot can be formed to have an opening at the exterior surface of proximal member that is narrower than the diameter of the needles (and optionally the pusher 126) while the internal portion or diameter of the slot can be dimensioned to permit facile movement of the needle therethrough. An exit opening is located at the distal end of channel 124.

Proximal member 112 includes a blood return line 125 that terminates in a fitting 127, for example, a luer lock that can be mated to a syringe. Alternatively, line 125 can terminate in a valve or shunt to control and stop blood flow therethrough. It is preferable that blood line 125 allow visible observation of blood originating from inside the vascular vessel. This can facilitate proper placement of the device for suturing.

Referring additionally to FIGS. 2 and 3, distal member 114 is sized and/or configured to be received within a lumen of a patient's vascular vessel similar to distal member 114. In additional embodiments, distal member 14 can be coated or impregnated with a lubricant, bioactive agent, such as an anticoagulant material, and the like. In certain embodiments, it is preferable that at least distal member 14 be formed of a flexible or elastomeric material that is biocompatible—particularly with blood. For example, distal member 14 can be composed of a biocompatible polymeric material commonly used for catheters, such as silicone rubber, polyethylene, polyolefin, polyurethane, polytetrafluoroethylene, polyvinyl chloride and the like.

Distal member 114 includes a receptacle 122 sized and configured to receive and retain at least one needle 118a, and preferably two or more needles 118b, 118c . . . . Preferably, receptacle 122 is sized to retain one or more needles such that the proximal end of each of the needles does not extend beyond opening 152.

A needle catching element 123 located in receptacle 122 is provided to engage with at least a portion of needles 118a, 118b, 118c . . . . Element 123 can be configured as a plug of pierceable material. The material can be any biocompatible material pierceable with a surgical needle. Representative examples include materials such as silicone rubber, polyethylene, or polyurethane. In certain embodiments, the plug of material is composed of the same material as that used to form the distal member. The plug of material can be friction fit, adhesively bound, or mechanically retained inside receptacle 122. In other embodiments, the plug of material can include a molded flap extending from an interior wall portion of receptacle 122. In still other embodiments, the needle catching element 123 can be integral with, or alternatively define, a bottom wall portion of receptacle 122. Needle capture element 123 can completely close off or block receptacle 122. In other forms, element 123 need not completely block receptacle 122.

Referring back to FIG. 1, distal member 14 can also include a lumen 139 extending at least partially therethrough. Preferably, lumen 139 is separate from receptacle 122. Lumen 139 can be provided to receive or follow a guide wire left in place after a particular diagnostic or treatment procedure. This can allow the facile insertion of distal member 114 into the patient's vascular vessel. In a preferred embodiment, lumen 139 exits through a side of distal member 114 at opening 140 to permit a guide wire (not shown) to extend out without interfering with the needles, needle path, or suture material. The guide wire can be removed after placement of the suture device or left in as desired or considered medically prudent by the surgeon.

Intermediate member 116 is located between proximal member 112 and distal member 114. Intermediate member 116 defines a tissue-receiving area 145. In the illustrated embodiment, intermediate member is configured to include an arcuate portion or a crooked section. The arcuate portion or crook can defines a concave interior surface 147 and a convex exterior surface 148. Intermediate member 116 includes a first opening 150 providing access from the channel 124 to the tissue receiving area 145 and a second opening 152 from the receptacle 122 providing to the tissue receiving area 145. Preferably, first and second openings 150 and 152 are linearly or axially aligned. Intermediate member 116 can be composed of a biocompatible material that is substantially resistant to deformation and therefore can maintain the linearity between channel 124 and receptacle/chamber 122 and the respective first and second openings 150 and 152. Examples of suitable materials include TEFLON, NYLON, polyamids, and the like.

Intermediate member 116 also includes means and structure for reliable positioning of the device during surgery to facilitate closing the vascular puncture wound with sutures. Part of the positioning structure includes an opening 154 providing fluid communication to blood return line 125 in proximal member 112. In a preferred embodiment, opening 154 is located on a portion of the convex surface 148 of the intermediate member 116 opposite the tissue receiving region 145. In use, with the distal member of the device suitably positioned within the lumen of a vascular vessel, opening 154 is also located in the interior of the lumen. This permits blood from the vessel to enter blood return line 125, which can then be visibly observed by the surgeon. If blood is not observed in blood return line 125, then the distal member may not have been inserted to a sufficient depth into the lumen of the vascular vessel.

Additionally, a ridge or stop 156 extends from the concave surface into the tissue receiving region. Stop 156 is configured to bear against vascular tissue adjacent the puncture wound. In a preferred embodiment, first opening 150 extends through a portion of stop 56 permitting needle 118 to pierce tissue adjacent thereto. Stop 156 is sized to bear against the vascular tissue and avert further insertion of the device 110 into the vascular vessel. When provided together, stop 156 and opening 150 with blood return line 125 cooperate to ensure accurate placement of the suturing device in the patient's vascular vessel. Ridge or stop 156 can also extend radially about the entire circumference of intermediate member 116.

FIG. 2 shows needle 118a entering opening 152 in distal member 114 and traversing receptical 122 in response to distal movement of needle pusher 126.

FIG. 3 illustrates the capture of needle 118a within receptacle 122. Element 123 is positioned in receptacle 122 to engage with at least the distal tip 132 of needle 118a. Preferably element 123 is positioned at a location or depth within receptacle 122 such that the proximal end 134 of a captured needle does not extend out of opening 152 of receptacle 122 to snag on any tissue or other structure as the suturing device is manipulated and eventually removed from the vascular vessel.

FIGS. 4 and 5 illustrate partial views of an alternative embodiment of a suturing device 210 with a needle capture element 223. The illustrated distal and intermediate members 214 and 216 are configured similarly to distal and intermediate members 114 and 116. However, distal member 214 includes a receptacle 222. Receptacle 222 is configured to receive one or more needles therein. Needle capture element 223 comprises at least one projection 229 and preferably at a second projection 231 each extending radially inwardly from an interior wall portion 233. It will be understood that receptacle 222 can include a plurality of projections similarly configured as illustrated and/or described for projections 229 and 231. The projections 229 and 231 are configured to engage and capture or retain one or more needles 218 within the interior of receptacle 222. The projections 229 and 231 can frictionally engage the tips or sides of inserted needles to prevent their accidental dislodgement during surgical manipulation. In the illustrated embodiment, projections 229 and 231 are configured as a plurality of paired leaves projecting from the interior wall portion 233 of receptacle 222. It will be understand that in other embodiments, the leaves need not be paired; or, if paired, the leaves can be axially and/or radially offset from each other. In still other embodiments, projections 229 and 231 can be configured as protuberances, bumps, ridges, or threads extending from an internal wall portion of receptacle 222 to engage and retain one or needles 218 therein. Further, one or more of needles 118a, 118b, and 118c can include a recessed surface configured for engagement with at least one of the projections 229 and 231. For example, a needle can be configured with a barbed point or alternative with a tip similar to a tip as described in copending U.S. patent application Ser. No. 11/199,515 filed on Aug. 8, 2005, (which is incorporated by reference herein.)

Referring specifically to FIG. 5, a needle 218 with a length of suture material 220 is illustrated as captured within lumen 222. As can be observed in the illustration, a plurality of projections 229 and 231 frictionally engage with the sides of the inserted needle 218. Preferably, the projections 229 and 231 are angled in the distal direction from their point of connection to wall 233 of receptical 222. This causes the frictional engagement resisting needle movement in a proximal direction to be greater than the frictional engagement resisting a needle movement in a distal direction. This engagement effectively prevents the inserted needle 218 from being dislodged by manipulation of suturing device 210 within the patient or upon withdrawing the suturing device from the vascular vessel.

Figure 6:
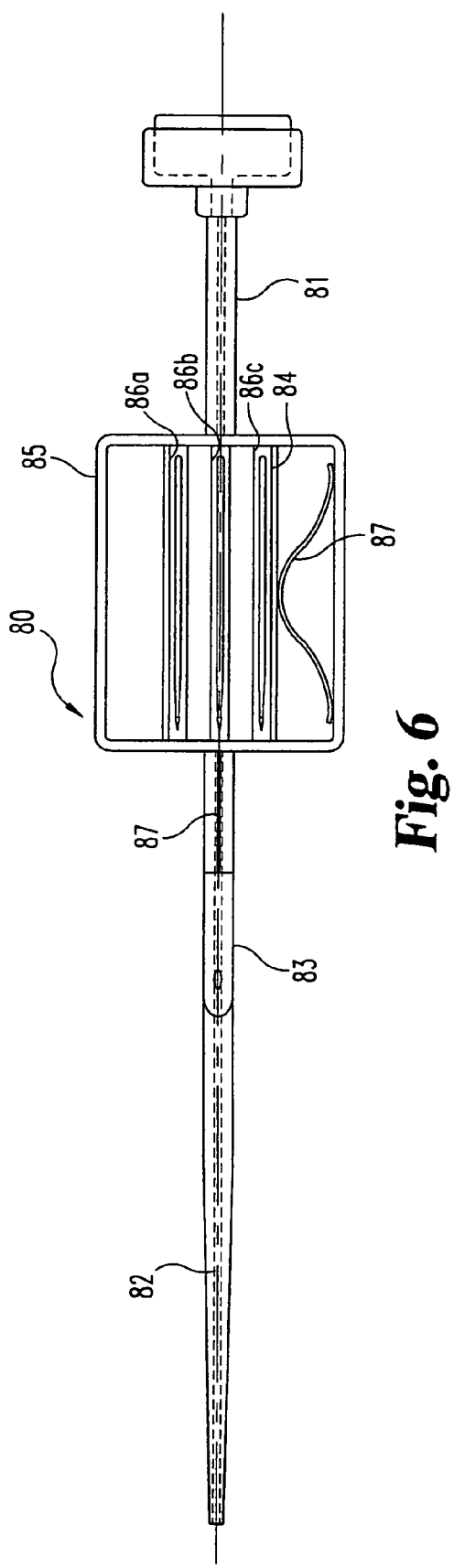
FIG. 6 is a perspective view of an alternative embodiment of a suturing device with a needle cartridge for use in accordance with the present invention.
Figure 7:
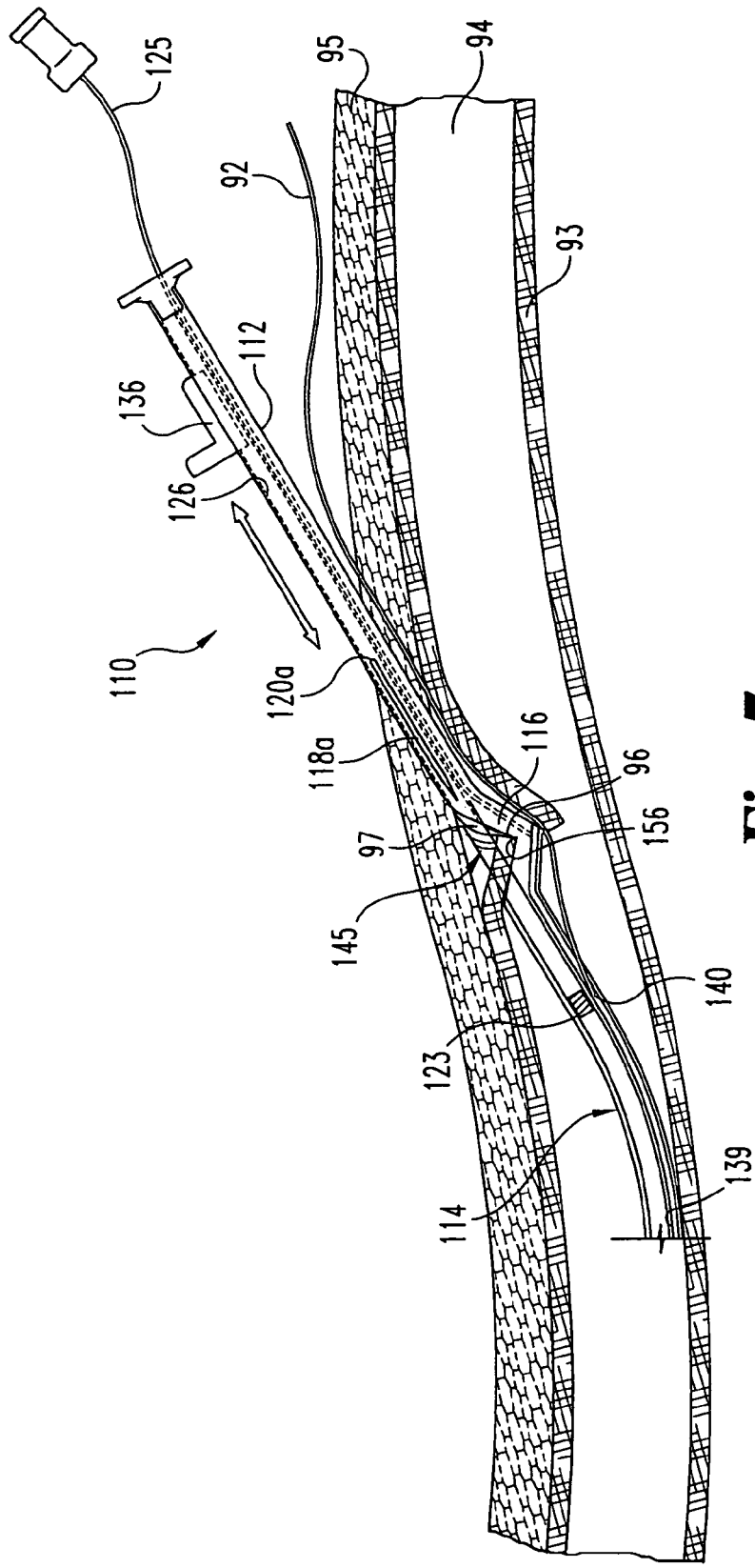
FIGS. 7-12 illustrate methods of use of the suturing device according to the present invention.

FIG. 6 is a perspective view of another embodiment of a suturing device 80 with a needle cartridge in accordance with the present invention. Device 80 includes a proximal member 81, a distal member 82, and an intermediate member 83 therebetween. Proximal member 81 includes a needle cartridge 84 slidably mounted in body 85. Needle cartridge 84 can include a plurality of needle slots, for example, two, three, four, or more slots 86a. 86b, 86c . . . , each for a separate needle. Each needle in needle cartridge 84 is individually advanceable through a central needle channel along a length of proximal member 81. Needle cartridge 84 is slidably disposed within body 85 to axially align the selected needle slot 86a. 86b, 86c . . . with a single needle channel 87. If desired, needle cartridge 84 can be biased to automatically align the successive needle slots with the needle channel after the preceding needle has been advanced along the channel. Alternatively, suturing device 80, body 85, and/or cartridge 84 can include one or more of ratchetings, positive stops, or locks to individually align the desired needle slot with the channel. In other embodiments, needle cartridge 84 can be provided as a revolving barrel that can hold two, three, or more needles in respective needle slots radially disposed about the barrel. The barrel can be rotatably mounted on or about proximal member 81. Distal member 82 and intermediate member 83 can be configured substantially as described above for members 114 and 116, respectively.

FIGS. 7 through 13, illustrate the use of suturing device 110 for closure of a puncture wound 96 in a vascular vessel 93. A puncture wound in a vascular vessel can be sutured closed using the suturing device 110. Suturing device 110 can be inserted distally into the vascular vessel. This can be accomplished with or without the use of a guide wire. In a procedure where a guide wire has been previously used, suturing device can be threaded onto a guide wire 92 which extends from internal vessel lumen 94 through wound 93 and a portion of the overlying tissue 95 to be exposed to the surgeon. In that regard, opening 140 of lumen 139 can be threaded onto guide wire 92 which then extends out through opening 140. Thus, the flexible portion of distal member 114 can be gingerly threaded into the lumen 94 of vessel 93. The distal member 114 of device 110 can be positioned within lumen 94 such that intermediate member 116 engages with a portion of the tissue surrounding puncture 96. Distal member 114 is advanced in a distal direction until blood is observed in blood return line 125. Additionally, when provided, stop 156 abuts or bears against the external surface of the vascular vessel. This can be detected by the increased resistance to further advancement of the device in the distal direction. Both blood return line 125 and stop 156 can be used to ascertain that the device has been correctly positioned within the lumen 94 of the vascular vessel 93 to allow suturing of puncture 96. It should be noted that observance of blood in needle channel 124 is an indication that device 110 has been inserted too far into the lumen 94 such that first opening 150 is exposed to the interior or blood side of vessel 93. If desired, guide wire 92 can then be withdrawn from lumen 139 and out of vascular vessel 93—if it is no longer needed for subsequent procedures.

After the distal member is positioned as desired, the vascular tissue adjacent the puncture wound is received within the tissue receiving area 145. As noted above, intermediate member 116 provides an essentially linear needle pathway between needle channel 124, receptacle 122, and the vascular tissue in the tissue receiving area 145. Consequently, when needle 118a is advanced through channel 124, it pierces the vascular tissue 93 at a first suture site 97 adjacent the puncture wound 96.

Figure 8:
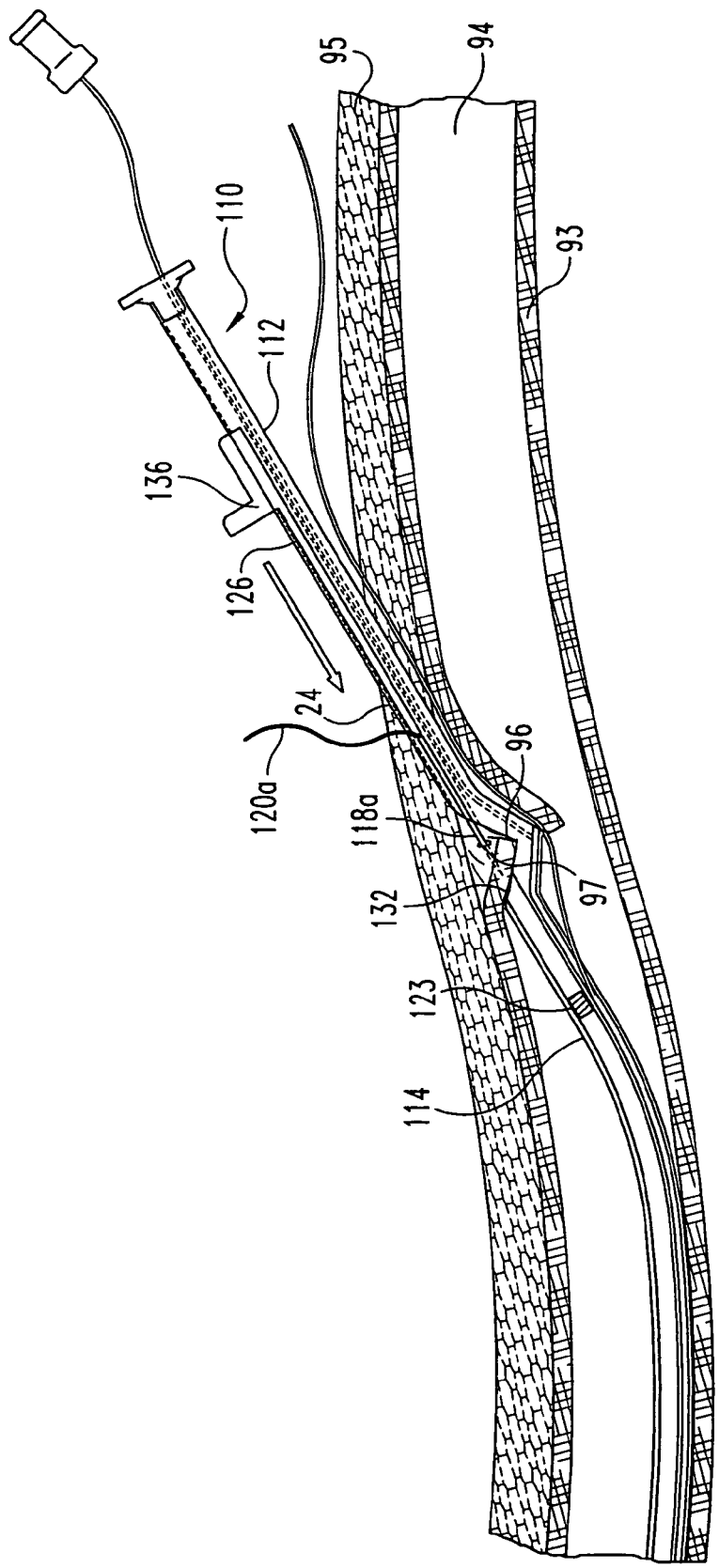

FIG. 8 illustrates suturing device 110 at a first suture position. Intermediate member 116 provides an essentially linear needle pathway between channel 124 and receptacle 122. A first needle 118a advancing through channel 124 using needle pusher 126 pierces vascular tissue in tissue receiving area 145 at the first suture site 97. Needle 118a trails a length of suture material 120a pulling it through the vascular at suture site 97 adjacent wound 96. From there, needle tip 132 is advanced into to receptacle 122 to engage needle capture element 123. Thereafter, needle 118a and optionally a portion of the suture material 120 are inserted into receptacle 122 where at least a portion of the needle 118a engages with needle capture element 123. Needle capture element 123 reliably retains needle 118a within receptacle 122 during the rest of the suturing procedure or until the surgeon decides to withdraw the needle.

Figure 9:
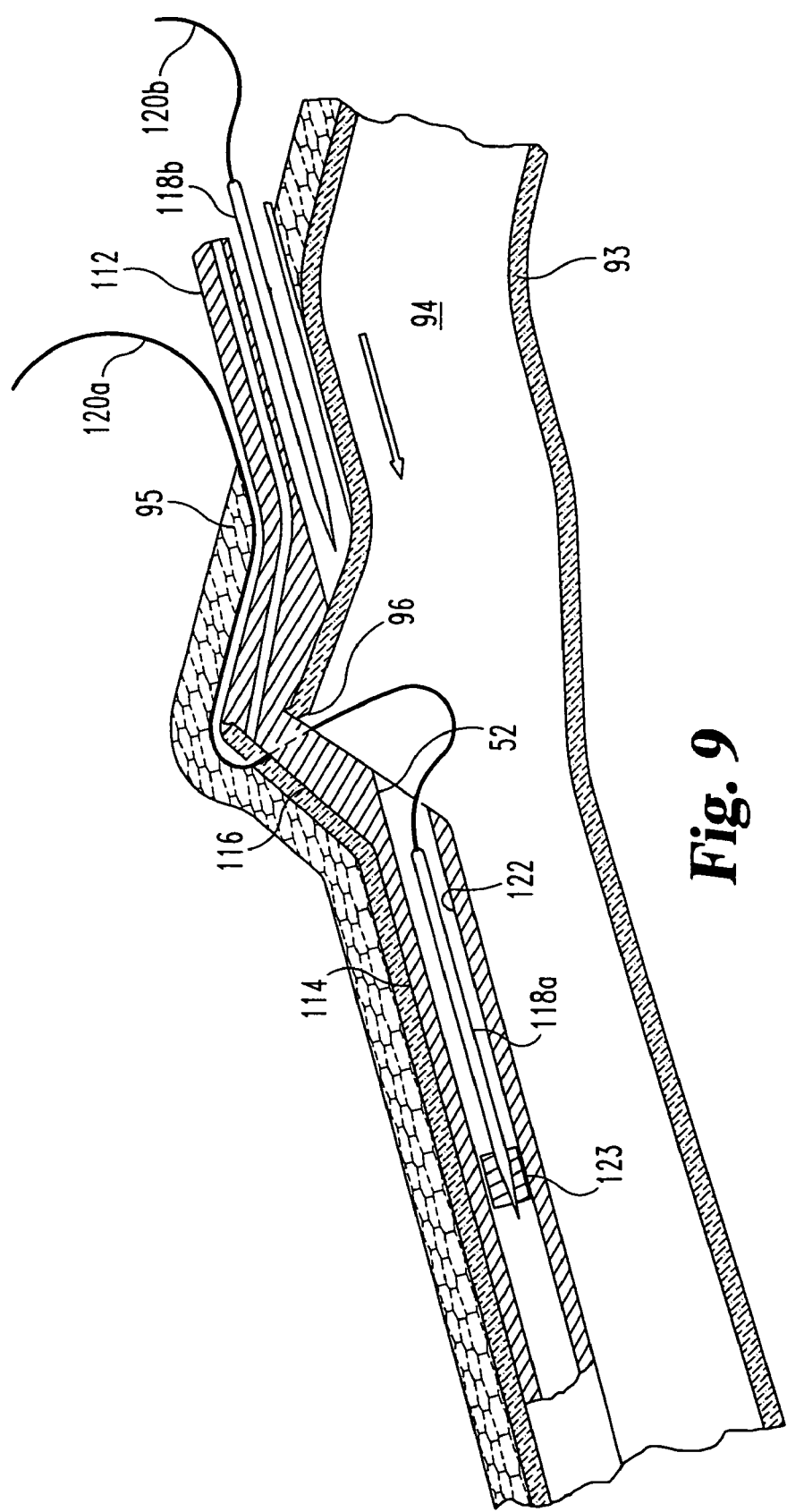

As shown in FIG. 9 suturing device 110 is rotated into a second suture position. Suture device 110 can be rotated approximately 180° so that in the second suture position, suture device 110 is positioned to operate on a second side of wound 96 diametrically opposite first suture site 97.

Figure 10:
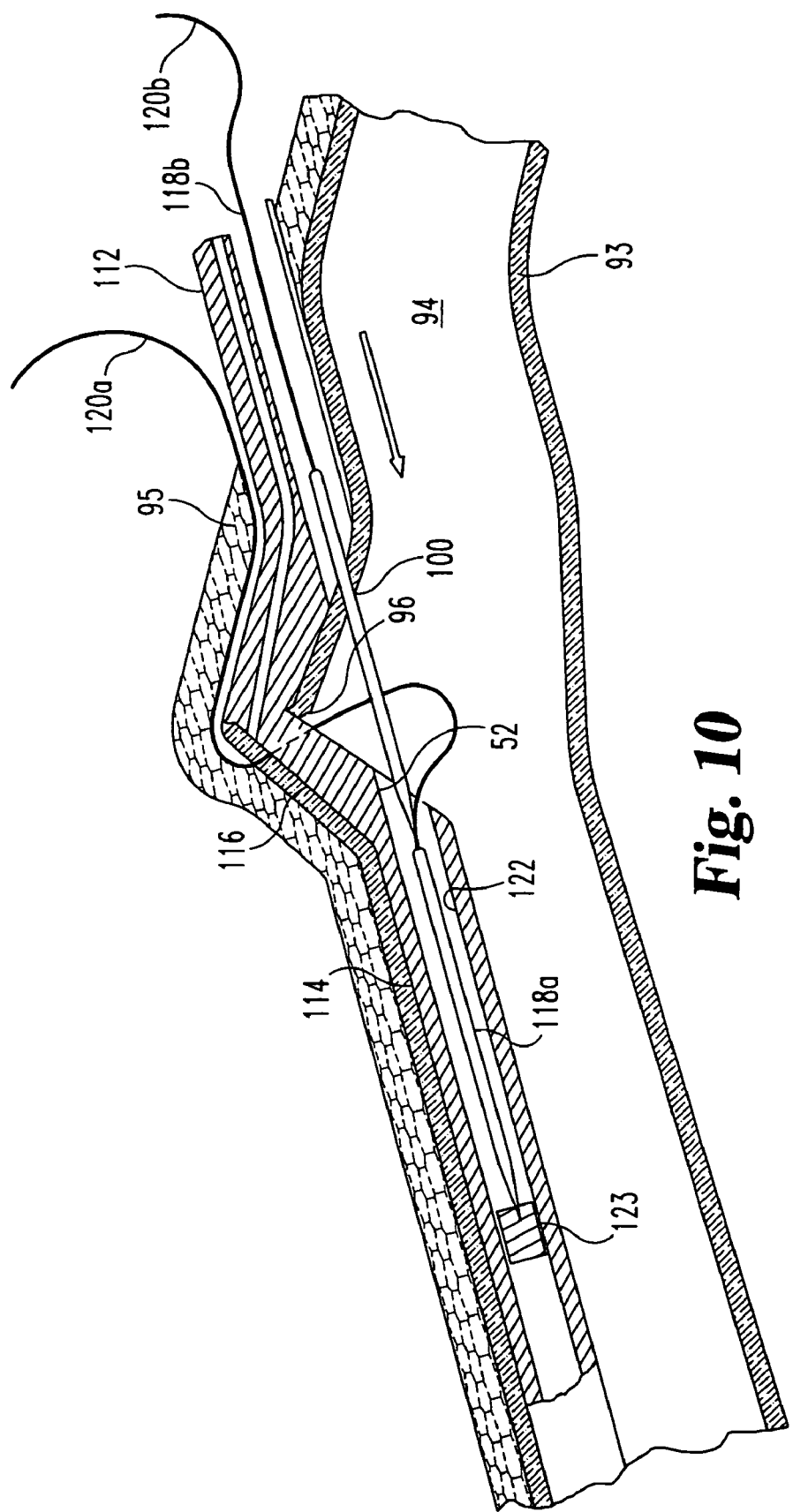

FIG. 10 illustrates suturing device 110 in the second suture position. A second needle 118b can be advanced through or along receptacle 122 using the needle pusher 126, either the same needle pusher or a second, different needle pusher. Needle 118b exits first opening 150 to pierce vascular tissue received in the tissue receiving area 145 at a second suture site 100. Continuing the advancement of needle 118b through the needle path draws the attached suture material 120b through second suture site 100 adjacent wound 96. Thereafter at least a portion of needle 118b is captured and retained by needle capture element 123 within receptacle 122. If desired, suturing device 110 can again be repositioned to draw suture material through a third and any desired subsequent suturing sites. It will be understood that suture material 120a and 120b can be opposite ends of the same piece of suture material. Alternatively, suture material 120a and 120b can be two separate lengths of suture material.

Figure 11:
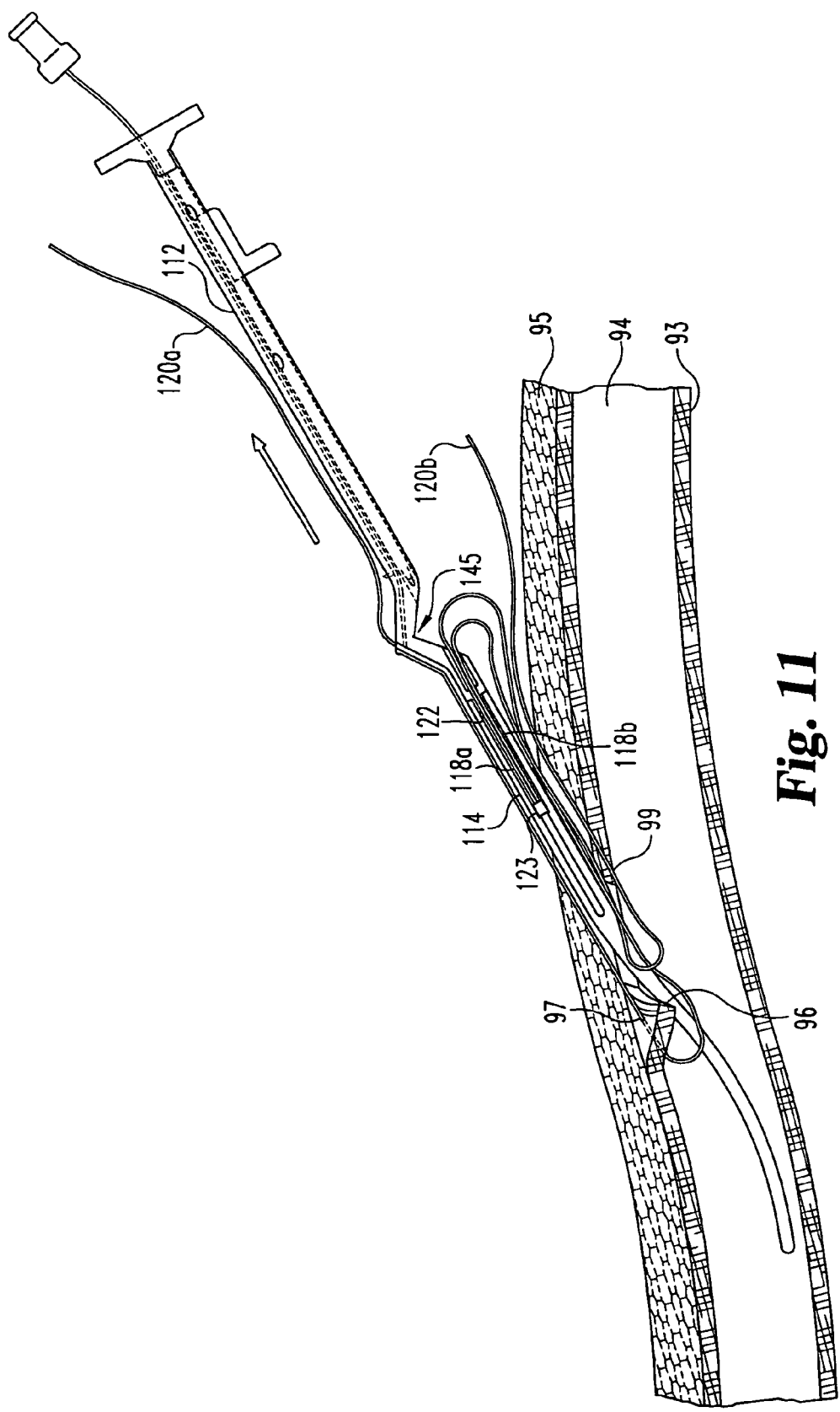
Figure 12:
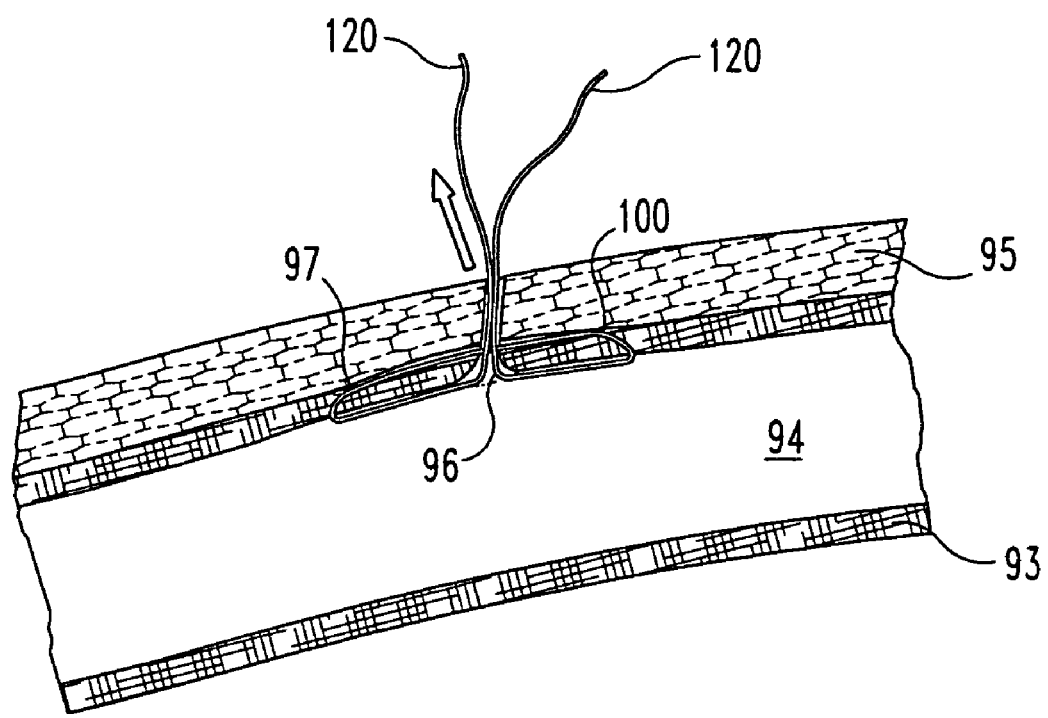

FIG. 11 illustrates device 110 being removed in a distal direction from vascular vessel 93. As suture device 110 is withdrawn in the distal direction, needles 118a and 118b remain embedded within the needle catching element 123 in receptacle 122. Consequently, the attached lengths of suture material 120a and 120b are pulled in a distal direction through the vascular tissue at the first and second suture sites 97 and 100, respectively and then out through the wound 96. One implementation of the suturing device can be a common length of suture material 120 attached to the proximal ends of needles 118a and 118b. As illustrated in FIG. 12, the resulting suture path extends from the proximal side of vessel 94 across the wound opening and through the first and second suture sites 97 and 100 into the lumen 94. The suture material 120 then extends out through wound opening 96 back to the distal side of vessel 93.

FIG. 12 depicts wound closure. The free ends of the suture material 120 can be gathered and a suture knot tied. As with the other procedures described above, a knot pusher 115, knot boxes as described in WO 01/19258, and knot replacement technologies (see FIGS. 13 and 14) can be used to close the wound and secure the suture material. The lengths of suture material can be gathered. The length of suture material can be separated from the needles. Pulling the lengths of suture material taut closes the wound in the vessel. A surgical knot can be tied securing the wound closure. A knot pusher, for example, the knot pushers described in U.S. Pat. No. 5,304,184 issued to Hathaway et al., U.S. Pat. No. 5,746,755 issued to Wood et al., and U.S. Pat. No. 6,132,439 issued to Kontos, can be used to advance the loosely tied knot to the exterior surface of the vascular vessel. In selected embodiments, the surgeon can then tie a suitable surgical knot using the respective lengths of suture material to close the puncture wound 96.

In other embodiments, the suture material can be secured using a variety of knot replacement technologies such as that disclosed in U.S. patent application Ser. No. 10/164,606 (US Patent Publication No. 2003/0229377) and in Ser. No. 10/305,923 (US Patent Publication No. 2004/0102809) and depicted in FIGS. 13 and 14. Each of the above-noted references are incorporated by reference in their entirety.

Figure 13:
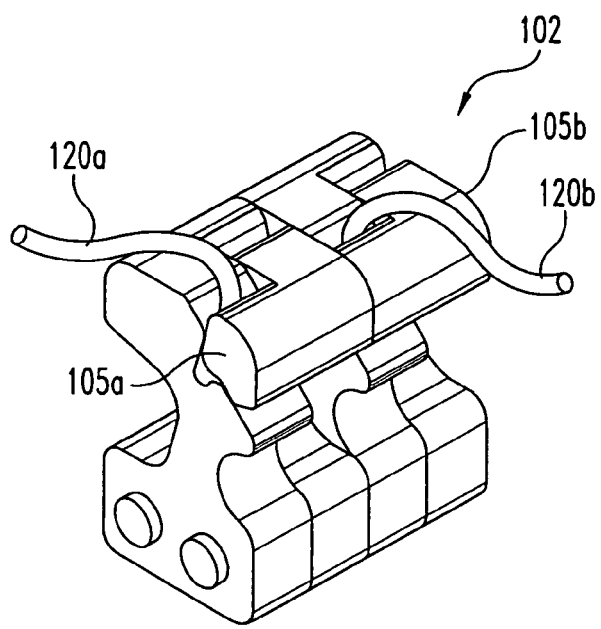
FIG. 13 is a perspective view of one embodiment of a suture securing device for use in the present invention.

FIG. 13 is a perspective view a suturing securing device 102 for use in the present invention. Suture securing device 102 is described and illustrated in US Patent Publication No. 2004/0102809 which is incorporated herein by reference. In use device 102 can secure ends of one, two, three or more lengths of suture material. Two lengths of suture material 120a and 120b are illustrated with device 102. The lengths of suture material are threaded into the flexible elements 105a and 105b which are then locked or fixed together securing the suture material therein.

Figure 14:
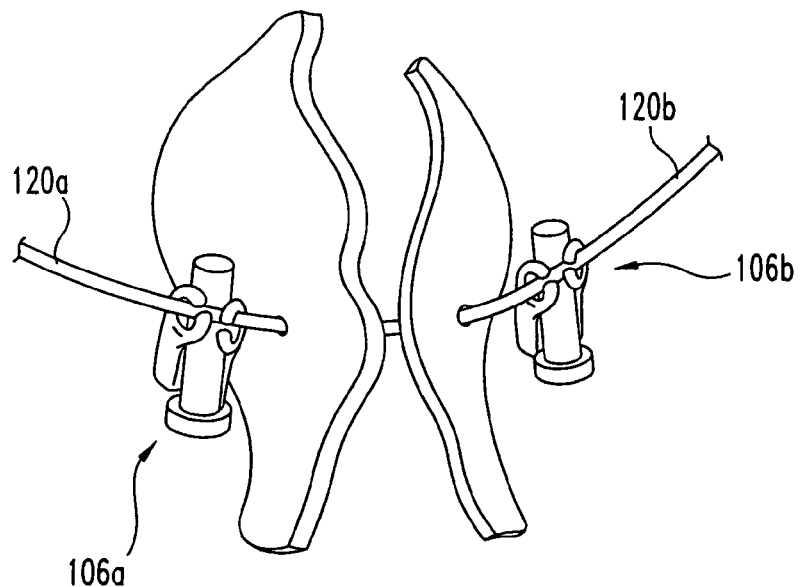
FIG. 14 is a perspective view of an alterative embodiment of a suture securing device for use in the present invention.

FIG. 14 is another embodiment of suture securing devices 106a and 106b for use in the present invention. Devices 106a and 106b are described in US Patent Publication No. 2003/0229377 which is incorporated herein by reference in its entirety. Devices 106a and 106b cooperate by separately clipping onto a selected length of suture material 104a or 104b which have previously pulled taut to close wound or complete the surgical procedure. The devices prevent the suture material from regressing back through the sutured tissue.

The present invention provides a variety of means, devices and methods for closing wounds in tissue and is particularly but not exclusively suitable for vascular tissue. It will be understood that the present invention contemplates modifications as would occur to those skilled in the art without departing from the spirit of the present invention. In addition, the various structures, elements, and procedural steps or stages have been described with reference to specified embodiments and devices. Each of the individual or a combination of the structures, elements, and procedural steps or stages are contemplated to be combinable with each of the other embodiments and devices described herein and as such are contemplated to be within the scope of the present invention.

All publications, patents, and patent applications cited in this specification are herein incorporated by reference as if each individual publication, patent, or patent application was specifically and individually indicated to be incorporated by reference and set forth in its entirety herein. Further, any theory of operation, proof, or finding stated herein is meant to further enhance understanding of the present invention and is not intended to make the scope of the present invention dependent upon such theory, proof, or finding.

What is claimed is:

1. A method of suturing vascular tissue adjacent an opening in a vascular vessel, said method comprising:
    inserting a suturing device through the opening in the vascular vessel, said suturing device comprising:
        a proximal member having a needle channel and a first needle and a second needle therein, said first needle and said second needle carrying a length of suture material;
        a distal member configured to be inserted into the lumen of the vascular vessel, the distal member having a receptacle comprising a needle capture element and being sized to receive said first needle and said second needle therein, the needle capture member including an interior wall portion and a first plurality of projections and a second plurality of projections, the first and second pluralities of projections extending at an angle away from the interior wall portion toward a distal end of the distal member, the first plurality of projections being longitudinally offset from the second plurality of projections; and
        an intermediate member disposed between the proximal member and the distal member, the intermediate member defining a tissue receiving area and configured to provide a linear needle pathway between the channel and the receptacle;
    advancing said first needle distally along the needle channel to pierce the vascular tissue and draw a portion of the length of suture material through the vascular tissue; and
    engaging said first needle with the needle capture element in the receptacle by inserting said first needle between the first and/or second plurality of projections.

2. The method of claim 1 comprising sequentially advancing at least said first needle and said second needle along the needle channel and into the receptacle.

3. The method of claim 1 comprising withdrawing the suturing device from the opening in the vascular vessel with said first needle retained within the receptacle.

4. The method of claim 3 comprising pulling suture material distally through vascular tissue adjacent the opening.

5. The method of claim 4 comprising pulling suture material proximally out the opening.

6. The method of claim 5 comprising pulling two lengths of suture material proximally out the opening.

7. The method of claim 6 comprising securing the two lengths of suture material together.

8. The method of claim 7 wherein said securing comprises tying the two lengths of suture material together.

9. The method of claim 7 wherein said securing comprises using a suture securing device to secure the two lengths of suture material together.

10. The method of claim 7 comprising using a knot pusher to secure the two lengths of suture material together.

11. The method of claim 1 further comprising rotating said suturing device from a first position to a second position.

12. The method of claim 1 further comprising:
    advancing said second needle distally along the needle channel to pierce the vascular tissue and draw a portion of the length of suture material through the vascular tissue; and
    engaging said second needle with the needle capture element in the receptacle.

13. The method of claim 1 wherein said first needle and said second needle share a common length of suture.

14. The method of claim 1 wherein said suturing device further comprises a guide wire lumen.

15. The method of claim 1 wherein said suturing device further comprises a locator.

16. The method of claim 15 wherein said locator further comprises a bleed back lumen.

17. The method of claim 1, wherein the first plurality of projections are all positioned at the different longitudinal location and distributed about the longitudinal axis.

18. The method of claim 1, wherein the first needle and the second needle both have a body that is substantially straight and wherein the first needle and the second needle each further comprise a distal tip that tapers inward from the substantially straight body.

19. The method of claim 1, wherein the first plurality of projections and the second plurality of projections cooperate to resist the proximal movement of both the first needle and the second needle.

20. A method of suturing vascular tissue adjacent an opening in a vascular vessel, said method comprising:
    inserting a suturing device through the opening in the vascular vessel, said suturing device comprising:
        a proximal member having a needle channel and a first needle and a second needle therein, said first needle and said second needle carrying a length of suture material, said first needle and said second needle both having a body that is substantially straight, said first needle and said second needle each further comprising a distal tip that tapers inward from the substantially straight body;

a distal member configured to be inserted into the lumen of the vascular vessel, the distal member having a receptacle comprising a needle capture element and being sized to receive said first needle and said second needle therein, the needle capture member including an interior wall portion and a first plurality of projections and a second plurality of projections, the first and second pluralities of projections extending at an angle away from the interior wall portion toward a distal end of the distal member, the first plurality of projections being longitudinally offset from the second plurality of projections; and an intermediate member disposed between the proximal member and the distal member, the intermediate member defining a tissue receiving area and configured to provide a linear needle pathway between the channel and the receptacle;

advancing said first needle distally along the needle channel to pierce the vascular tissue and draw a portion of the length of suture material through the vascular tissue;

engaging said first needle with the needle capture element in the receptacle;

following advancing said first needle distally along the needle channel and engaging said first needle with the needle capture element, rotating said suturing device from a first position to a second position;

following rotating said suturing device from a first position to a second position, advancing said second needle distally along the needle channel to pierce the vascular tissue and draw a portion of the length of suture material through the vascular tissue and engaging said second needle with the needle capture element in the receptacle.

21. The method of claim 20, wherein the first plurality of projections are all positioned at the different longitudinal location and distributed about the longitudinal axis.

22. The method of claim 20, wherein the first needle and the second needle both have a body that is substantially straight and wherein the first needle and the second needle each further comprise a distal tip that tapers inward from the substantially straight body.

23. The method of claim 20, wherein the first plurality of projections and the second plurality of projections cooperate to resist the proximal movement of both the first needle and the second needle.

* * * * *